US007250294B2

(12) United States Patent
Carpenter et al.

(10) Patent No.: US 7,250,294 B2
(45) Date of Patent: Jul. 31, 2007

(54) SCREENING SMALL MOLECULE DRUGS USING NEURAL CELLS DIFFERENTIATED FROM HUMAN EMBRYONIC STEM CELLS

(75) Inventors: Melissa K. Carpenter, Castro Valley, CA (US); Jerrod J. Denham, San Francisco, CA (US); Margaret S. Inokuma, San Jose, CA (US); R. Scott Thies, Pleasanton, CA (US)

(73) Assignee: Geron Corporation, Menlo Park, CA (US)

(*) Notice: Subject to any disclaimer, the term of this patent is extended or adjusted under 35 U.S.C. 154(b) by 391 days.

(21) Appl. No.: 10/157,288

(22) Filed: May 28, 2002

(65) Prior Publication Data

US 2003/0103949 A1    Jun. 5, 2003

Related U.S. Application Data

(63) Continuation-in-part of application No. 09/888,309, filed on Jun. 21, 2001, now abandoned, and a continuation-in-part of application No. 09/872,183, filed on May 31, 2001, now Pat. No. 6,833,269, and a continuation-in-part of application No. 09/859,351, filed on May 16, 2001, now abandoned.

(60) Provisional application No. 60/257,608, filed on Dec. 22, 2000, provisional application No. 60/213,739, filed on Jun. 22, 2000, provisional application No. 60/205,600, filed on May 17, 2000.

(51) Int. Cl.
*C12N 5/00* (2006.01)
*C12N 5/02* (2006.01)

(52) U.S. Cl. .................................................... 435/377
(58) Field of Classification Search ............... 435/325, 435/363, 366, 368, 375, 377
See application file for complete search history.

(56) References Cited

U.S. PATENT DOCUMENTS

| | | | |
|---|---|---|---|
| 5,639,618 A | 6/1997 | Gay | 435/7.21 |
| 5,672,499 A | 9/1997 | Anderson et al. | 435/240.4 |
| 5,766,948 A | 6/1998 | Gage et al. | 435/368 |
| 5,773,255 A | 6/1998 | Laurance et al. | 435/70.3 |
| 5,789,246 A | 8/1998 | Reid et al. | 435/325 |
| 5,849,553 A | 12/1998 | Anderson et al. | 435/172.3 |
| 5,851,832 A | 12/1998 | Weiss et al. | 435/368 |
| 5,928,947 A | 7/1999 | Anderson et al. | 435/455 |
| 5,968,829 A | 10/1999 | Ruddick et al. | 435/467 |
| 5,981,165 A | 11/1999 | Weiss et al. | 435/4 |
| 6,040,180 A | 3/2000 | Johe | 435/377 |
| 6,090,622 A | 7/2000 | Gearhart et al. | 435/366 |
| 6,200,806 B1 | 3/2001 | Thomson | 435/366 |
| 6,238,922 B1 | 5/2001 | Uchida | 435/380 |
| 6,458,589 B1 | 10/2002 | Rambhatla et al. | 435/370 |
| 6,602,711 B1 | 8/2003 | Thomson et al. | 435/378 |
| 6,833,269 B2 | 12/2004 | Carpenter | 435/377 |
| 2002/0009743 A1 | 1/2002 | Carpenter | 435/6 |
| 2002/0012903 A1 | 1/2002 | Goldman et al. | 435/4 |
| 2002/0151056 A1 | 10/2002 | Sasai et al. | 435/368 |
| 2004/0023376 A1 | 2/2004 | Thomson et al. | 435/366 |

FOREIGN PATENT DOCUMENTS

| | | |
|---|---|---|
| EP | 1022330 | 7/2000 |
| WO | WO 94/03199 | 2/1994 |
| WO | WO 98/50526 | 11/1998 |
| WO | WO 99/01159 | 1/1999 |
| WO | WO 99/04775 | 2/1999 |
| WO | WO 99/20741 | 4/1999 |
| WO | WO 99/28443 | 6/1999 |
| WO | WO 99/43785 | 9/1999 |
| WO | WO 99/53021 | 10/1999 |
| WO | WO 99/53022 | 10/1999 |
| WO | WO 00/17323 | 3/2000 |
| WO | WO 00/47762 | 8/2000 |
| WO | WO 01/51616 | 7/2001 |
| WO | WO 01/68815 | 9/2001 |
| WO | WO 01/83715 | 11/2001 |
| WO | WO 01/98463 | 12/2001 |
| WO | WO 02/081663 | 10/2002 |
| WO | WO 02/086106 | 10/2002 |
| WO | WO 2004/007696 | 1/2004 |

OTHER PUBLICATIONS

Lodish, ed., et al. (2000) Molecular Cell Biology, 4th Edition. (W.H. Freeman, New York), p. 968.*
Schuldiner et al. (2000) Effects of eight growth factors on the differentiation of cells derived from human embryonic stem cells. Proc. Natl. Acad. Sci. USA 97(21): 11307-11312.*
Verfaillie et al. (2002) Stem cells: Hype and reality. 2002: 369-391.*
Andrews, et al., Retinoic Acid Induces Neuronal Differentiation of a Cloned Haman Embryonal Carcinoma Cell Line in Vitro, Dev. Biol. 103:285 (1984).
Bain, et al., Embryonic Stem Cells Express Neuronal Properties in Vitro, Dev. Biol. 168:342 (1995).
Bain, et al., Retinoic Acid Promotes Neural and Represses Mesodermal Gene Expression in Mouse Embryonic Stem Cells in Culture, Chem. and Biophys. Res. Comm. 223:691 (1996).
Bain, et al., Neural Cells Derived by In Vitro Differentiation of P19 and Embryonic Stem Cells, Perspectives Dev. Neurobio. 5:175 (1998).

(Continued)

*Primary Examiner*—Anne-Marie Falk
(74) *Attorney, Agent, or Firm*—Bart W. Wise

(57) ABSTRACT

This invention provides populations of neural progenitor cells and differentiated neurons, obtained by culturing pluripotent cells in special growth cocktails. The technology can be used to produce progenitors that proliferate through at least ~40 doublings, while maintaining the ability to differentiate into a variety of different neural phenotypes, including dopaminergic neurons. The neural progenitors and terminally differentiated neurons of this invention can be generated in large quantities for use in drug screening and the treatment of neurological disorders.

16 Claims, 8 Drawing Sheets

OTHER PUBLICATIONS

Bodnar, et al., Extension of Life-span by Introduction of Telomerase into Normal Human Cells, Science 279:349 (1998).

Brustle, et al., In Vitro-Generated Neural Precursors Participate in Mammalian Brain Development, Proc. Natl. Acad. Sci. USA 94:14809 (1997).

Brustle, et al., Embryonic Stem Cell-Derived Glial Precursors: A Source of Myelinating Transplants, Science 285:754 (1999).

Clarke, et al., Generalized Potential of Adult Neural Stem Cells, Science 288:1660 (2000).

Deacon, et al., Blastula-Stage Stem Cells Can Differentiate into Dopaminergic and Serotonergic Neurons after Transplantation, Exp. Neurol. 149:28 (1998).

Fraichard, et al., In Vitro Differentiationof Embryonic Stem Cells into Glial Cells and Functional Neurons, J. Cell Science 108:3181 (1995).

Kalyani, et al., Cell Lineage in the Developing Neural Tube, Biochem. Cell Biol. 76:1051 (1998).

Lee, et al., Efficient Generation of Midbrain and Hindbrain Neurons from Mouse Embryonic Stem Cells, Nat. Biotechnol. 18:675 (2000).

Li, et al., Generation of Purified Neural Precursors from Embryonic Stem Cells by Lineage Selection, Curent Biology 8:971.

Ling, et al., Differentiation of Mesencephalic Progenitor Cells into Dopaminergic Neurons by Cytokines, Exp. Neurol. 149:411 (1998).

Liu, et al., Embryonic Stem Cells Differentiate into Oligodendrocytes and Myelinate in Culture and After Spinal Cord Transplantation, PNAS 97:6126 (2000).

Mayer-Prosche, et al., Isolation of Lineage-Restricted Neuronal Precursors from Mltipotent Neuroepithelial Stem Cells, Neuron 19:773 (1997).

McDonald, et al., Transplanted Embryonic Stem Cells Survive, Differentiate and Promote Recovery in Injured Rat Spinal Cord, Nat. Med. 5:1410 (1999).

Mujtaba, et al., Lineage-Restricted Neural Precursors Can Be Isolated from Both the Mouse Neural Tube and Cultured ES Cells, Dev. Biol. 214:113 (1999).

Okabe, et al., Development of Neuronal Precursor Cells and Funcitonal Postmitotic Neurons from Embryonic Stem Cells in Vitro, Mechanisms of Dev. 59:89 (1996).

Reubinoff, et al., Embryonic Stem Cell Lines From Human BlastoCysts: Somatic Differentiation In Vitro, Nature Biotechnol. 18:399 (2000).

Shamblott, et al., Derivation of Pluripotent Stem Cells From Cultured Human Primordial Germ Cells, Proc. Natl. Acad. Sci. USA 95:13726 (1998).

Strubing, et al., Differentiationof Pluripotent Embryonic Stem Cells into the Neuronal Lineage in Vitro Gives Rise to Mature Inhibitory and Excitatory Neurons, Mechanisms of Dev. 53"275 (1995).

Thomson, et al., Neural Differentiation of Rhesus Embryonic Stem Cells, APMIS 106:149 (1998).

Thomson, et al., Embryonic Stem Cell Lines Derived from Human Blastocysts, Science 282:1145 (1998).

Tropepe, et al., Autonomous Neural Cell Fate Specification in Mouse Embryonic Stem Cells—Abstract, Society for Neuroscience 25:527 (1999).

van Inzen, et al., Meuronal Differentiation of Embryonic Stem Cells, Biochimica et Biophsica Acta 1312:21 (1996).

Wagner, et al., Induction of a Midbrain Dopaminergic Phenotype in Nurr1-overexpressing Neural Stem Cells by Type 1 Astrocytes, Nature Biotechnol. 17:653 (1999).

Yao, et al., Neuronal Differentiation of P19 Embryonal Carcinoma cells in Defined Media, J. Neuroscience Res. 41:792 (1995).

Neural Implant Technologies, NeuroInvestment (Dec. 1999).

Lamb, T.M., et al., Neural Induction by the Secreted Polypeptide Noggin, Science 262:713 (1993).

Lim, D.A., et al., Noggin Antagonizes BMP Signaling to Create a Niche for Adult Neurogenesis, Neuron 27:713 (2000).

Sasal, Y., et al., Regulation of Neural Induction by the Chd and Bmp-4 Antagonistic Patturning Signals in Zenopus Nature 376:333 (1995).

Kalyani, A., et al., Cell Lineage in the Developing Neural Tube, Biochem. Cell Biol. 76:1051 (1998).

Li, M., et al., Generation of Purified Neural precursors from Embryonic Stem Cells by Lineage Selection, Current Biol., Current Science 8:971 (1998).

Mujtaba, T., et al., Lineage-Restricted Neural Precursors Can Be Isolated from Both the Mouse Neural Tube and Cultured ES Cells, Dev. Biol. 214:113 (1999).

Juul, et al., Erythropoietin and Erythropoietin Receptor in the Developing Human Central Nervous System, Pediatric Research 43:40 (1998).

Erythropoietin Regulates the In Vitro and In Vivo Production of Neuronal Progenitors by Mammalian Forebrain Neural Stem Cells, J. Neuroscience 21:9733 (2001).

Studer, L., et al., Enhanced Proliferation, Survival, and Dopaminergic Differentiation of CNS Precursors in Lowered Oxygen, J. Neuroscience 20:7377 (2000).

Kawasaki, et al., Generation of dopaminergic neurons and pigmented epithelia from primate IS cells by stromal cell-derived inducing activity, PNAS 99:1580 (2002).

Bain G et al, Expression of Retinoid X Receptors in P19 Embryonal Carcinoma Cells and Embryonic Stem Cells, Biochem Biophys Res Comm 200(3):1252 (1994).

Biesecker LG et al, Interleukin-6 is a Component of Human Umbilical Cord Serum and Stimulates Hematopoiesis in Embryonic Stem Cells in Vitro, Exp Hematol 21:774 (1993).

Bouwmeester T et al, Vertebrate Head Induction by Anterior Primitive Endoderm, BioEssays 19(10):855 (1997).

Burkert U et al, Early Fetal Hematopoietic Development from In Vitro Differentiated Embryonic Stem Cells, New Biol 3(7):698 (1991).

Carpenter MK et al, Enrichment of Neurons and Neural Precursors from Human Embryonic Stem Cells, Exp Neurol 172:383 (2001).

Chitnis A et al, Neural Induction and Neurogenesis in Amphibian Embryos, Perspectives Dev Neurobiol 3(1):3 (1995).

Davidson BP et al, Cell Fate and Lineage Specification in the Gastrulating Mouse Embryo, Cell Lineage & Fate Determination 33:491 (1999).

Dinsmore J et al, Embryonic Stem Cells Differentiated in Vitro as a Novel Source of Cells for Transplantation, Cell Transpl 5(2):131 (1996).

Fisher JP et al, Factors Influencing the Differentiation of Embryonal Carcinoma and Embryo-Derived Stem Cells, Exp Cell Res 182:403 (1989).

Gendron RL et al, Induction of Embryonic Vasculogenesis by bFGF and LIF in Vitro and in Vivo, Dev Biol 177:332 (1996).

Itskovitz-Eldor J et al, Differentiation of Human Embryonic Stem Cells into Embryoid Bodies Comprising the Three Embryonic Germ Layers, Mol Med 6(2):88 (2000).

Juul SE et al, Erythropoietin and Erythropoietin Receptor in the Developing Human Central Nervous System, Pediatric Res 43(1):40 (1998).

Keller GM, In Vitro Differentiation of Embryonic Stem Cells, Curr Opin Cell Biol 7:862 (1995).

Levinson-Dushnik M et al, Involvement of Hepatocyte Nuclear Factor 3 in Endoderm Differentiation of Embryonic Stem Cells, Mol Cell Biol 17(7):3817 (1997).

Mayer-Proschel M et al, Isolation of Lineage-Restricted Neuronal Precursors from Multipotent Neuroepithelial Stem Cells, Neuron 19:773 (1997).

Mummery CL et al, Characteristics of Embryonic Stem Cell Differentiation: A Comparison with Two Embryonal Carcinoma Cell Lines, Cell Diff Dev 30:195 (1990).

Odorico JS et al, Multilineage Differentiation from Human Embryonic Stem Cell Lines, Stem Cells 19:193 (2001).

O'Shea KS, Embryonic Stem Cell Models of Development, Anat Rec (New Anat) 257:32 (1999).

Pedersen RA, Studies of in Vitro Differentiation with Embryonic Stem Cells, Reprod Fertil Dev 6:543 (1994).

Pleasure SJ et al, NTera 2 Cells: A Human Cell Line which Displays Characteristics Expected of a Human Committed Neuronal Progenitor Cell, J Neurosci Res 35:385 (1993).

Rao MS, Multipotent and Restricted Precursors in the Central Nervous System, Anat Rec (New Anat) 257:1 (1999).

Rathjen J et al, Formation of a Primitive Ectoderm Like Cell Population, EPL Cells, From ES Cells in Response to Biologically Derived Factors, J Cell Sci 112:601 (1999).

Rathjen PD et al, Properties and Uses of Embryonic Stem Cells: Prospects for Application to Human Biology and Gene Therapy, Reprod Fertil Dev 10:31 (1998).

Robertson EJ, Derivation and Maintenance of Embryonic Stem Cell Cultures, Meth Mol Biol 75:173 (1997).

Schuldiner M et al, Effects of Eight Growth Factors on the Differentiation of Cells Derived from Human Embryonic Stem Cells, PNAS 97(21):11307 (2000).

Seaberg RM et al, Neural Determination Genes Revealed by Expression Trapping in Embryonic Stem Cells, Soc Neurosci (29th Annual Meeting) 25:527 No. 205.17 (1999).

Shingo T et al, Erythropoietin Regulates the in Vitro and in Vivo Production of Neuronal Progenitors by Mammalian Forebrain Neural Stem Cells, J Neurosci 21(24):9733 (2001).

Smith AG, Culture and Differentiation of Embryonic Stem Cells, J Tiss Cult Meth 13:89 (1991).

Studer L et al, Enhanced Proliferation, Survival, and Dopaminergic Differentiation of CNS Precursors in Lowered Oxygen, J Neurosci 20(19):7377 (2000).

Trojanowski JQ et al, Transfectable and Transplantable Postmitotic Human Neurons: A Potential "Platform" for Gene Therapy of Nervous System Diseases, Exp Neurol 144:92 (1997).

Varlet I et al, *Nodal* Expression in the Primitive Endoderm is Required for Specification of the Anterior Axis During Mouse Gastrulation, Development 124:1033 (1997).

Wang S et al, Neural Cells Derived in Culture from Human Embryonic Germ (EG) Cells, Mol Biol Cell 9:437A (1998) Abstract XP-001015834 (2535).

Wojcik BE et al, Catecholaminergic Neurons Result from Intracerebral Implantation of Embryonal Carcinoma Cells, Proc Natl Acad Sci USA 90:1305 (1993).

Yandava BD et al, "Global" Cell Replacement is Feasible via Neural Stem Cell Transplantation: Evidence from the Dysmyelinated *Shiverer* Mouse Brain, Proc Natl Acad Sci USA 96:7029 (1999).

Zhang SC et al, In Vitro Differentiation of Transplantable Neural Precursors from Human Embryonic Stem Cells, Nat Biotech 19:1129 (2001).

Zhou J et al, Induction of Tyrosine Hydroxylase Gene Expression in Human Foetal Cerebral Cortex, Neurosci Lttrs 252:215 (1998).

Ginis I et al, Differences Between Human and Mouse Embryonic Stem Cells, Dev Biol 269:360 (2004).

Li M et al, Lineage Selection and Isolation of Neural Precursors from Embryonic Stem Cells, Symposium Soc Experi Biol 53(29) (2001).

Sato N et al, Molecular Signature of Human Embryonic Stem Cells and its Comparison with the Mouse, Dev Biol 260:404 (2003).

\* cited by examiner

NCAM-positive cells

A2B5-positive cells

Treatment B

Treatment D

Treatment F

SCREENING SMALL MOLECULE DRUGS USING NEURAL CELLS DIFFERENTIATED FROM HUMAN EMBRYONIC STEM CELLS

REFERENCE TO RELATED APPLICATIONS

This application claims priority to U.S. Provisional Patent Applications 60/205,600, filed May 17, 2000; U.S. Ser. No. 60/213,739, filed Jun. 22, 2000; and 60/257,608, filed Dec. 22, 2000. This application also claims priority to International Application PCT/US01/15861, filed on May 16, 2001, designating the U.S. and published on Nov. 22, 2001 as WO 01/88104. This application is a continuation-in-part of U.S. utility patent application Ser. Nos. 09/859,351, filed on May 16, 2001, now abandoned; 09/872,183, filed on May 31, 2001, now U.S. Pat. No. 6,833,269; and 09/888,309, filed on Jun. 21, 2001, now abandoned.

All seven priority applications are hereby incorporated herein by reference in their entirety, along with International Patent Publication WO 01/51616.

TECHNICAL FIELD

This invention relates generally to the field of cell biology of embryonic cells and neural progenitor cells. More specifically, this invention relates to the directed differentiation of human pluripotent stem cells to form cells of the neuronal and glial lineages, using special culture conditions and selection techniques.

BACKGROUND

Repairing the central nervous system is one of the frontiers that medical science has yet to conquer. Conditions such as Alzheimer's disease, Parkinson's disease, epilepsy, Huntington's disease, and stroke can have devastating consequences for those who are afflicted. Traumatic injury to the head or the spinal cord can instantly propel someone from the bounds of everyday life into the ranks of the disabled.

What makes afflictions of the nervous system so difficult to manage is the irreversibility of the damage often sustained. A central hope for these conditions is to develop cell populations that can reconstitute the neural network, and bring the functions of the nervous system back in line.

For this reason, there is a great deal of evolving interest in neural progenitor cells. Up until the present time, it was generally thought that multipotent neural progenitor cells commit early in the differentiation pathway to either neural restricted cells or glial restricted cells. These in turn are thought to give rise to mature neurons, or to mature astrocytes and oligodendrocytes. Multipotent neural progenitor cells in the neural crest also differentiate to neurons, smooth muscle, and Schwann cells. It is hypothesized that various lineage-restricted precursor cells renew themselves and reside in selected sites of the central nervous system, such as the spinal cord. Cell lineage in the developing neural tube has been reviewed in the research literature by Kalyani et al. (Biochem. Cell Biol. 6:1051,1998).

Putative multipotent neuroepithelial cells (NEP cells) have been identified in the developing spinal cord. Kalyani et al. (Dev. Biol. 186:202, 1997) reported NEP cells in the rat. Mujtaba et al. (Dev. Biol. 214:113, 1999) reported NEP cells in the mouse. Differentiation of NEP cells is thought to result in formation of restricted precursor cells having characteristic surface markers.

Putative neural restricted precursors (NRP) were characterized by Mayer-Proschel et al. (Neuron 19:773, 1997). These cells express cell-surface PS-NCAM, a polysialylated isoform of the neural cell adhesion molecule. They reportedly have the capacity to generate various types of neurons, but do not form glial cells.

Putative glial restricted precursors (GRPs) were identified by Rao et al. (Dev. Biol. 188:48, 1997). These cells apparently have the capacity to form glial cells but not neurons.

Ling et al. (Exp. Neurol. 149:411, 1998) isolated progenitor cells from the germinal region of rat fetal mesencephalon. The cells were grown in EGF, and plated on poly-lysine coated plates, whereupon they formed neurons and glia, with occasional tyrosine hydroxylase positive (putative dopaminergic) cells, enhanced by including IL-1, IL-11, LIF, and GDNF in the culture medium.

Wagner et al. (Nature Biotechnol. 17:653, 1999) reported cells with a ventral mesencephalic dopaminergic phenotype induced from an immortalized multipotent neural stem cell line. The cells were transfected with a Nurr1 expression vector, and then cocultured with VM type 1 astrocytes. Over 80% of the cells obtained were claimed to have a phenotype resembling endogenous dopaminergic neurons.

Mujtaba et al. (supra) reported isolation of NRP and GRP cells from mouse embryonic stem (mES) cells. The NRPs were PS-NCAM immunoreactive, underwent self-renewal in defined medium, and differentiated into multiple neuronal phenotypes. They apparently did not form glial cells. The GRPs were A2B5-immunoreactive, and reportedly differentiated into astrocytes and oligodendrocytes, but not neurons.

A number of recent discoveries have raised expectations that embryonic cells may become a pluripotential source for cells and tissues useful in human therapy. Pluripotent cells are believed to have the capacity to differentiate into essentially all types of cells in the body (R. A. Pedersen, Scientif. Am. 280(4):68, 1999). Early work on embryonic stem cells was done using inbred mouse strains as a model (reviewed in Robertson, Meth. Cell Biol. 75:173, 1997; and Pedersen, Reprod. Fertil. Dev. 6:543, 1994).

Compared with mouse ES cells, monkey and human pluripotent cells respond quite differently to culture conditions, and require different factors to be propagated in an undifferentiated state. Only recently have discoveries been made that allow primate embryonic cells to be cultured ex vivo.

Thomson et al. (Proc. Natl. Acad. Sci. USA 92:7844, 1995) were the first to successfully culture embryonic stem cells from primates, using rhesus monkeys and marmosets as a model. They subsequently derived human embryonic stem (hES) cell lines from human blastocysts (Science 282:114, 1998). Gearhart and coworkers derived human embryonic germ (hEG) cell lines from fetal gonadal tissue (Shambloft et al., Proc. Natl. Acad. Sci. USA 95:13726, 1998). Both hES and hEG cells have the long-sought characteristics of human pluripotent stem (hPS) cells: they are capable of ongoing proliferation in vitro without differentiating, they retain a normal karyotype, and they retain the capacity to differentiate to produce all adult cell types.

Reubinoff et al. (Nature Biotechnol. 18:399, 2000) reported somatic differentiation of human blastocysts. The cells differentiated spontaneously in culture, with no consistent pattern of structural organization. After culturing for 4-7 weeks to high density, multicellular aggregates formed above the plane of the monolayer. Different cells in the culture expressed a number of different phenotypes, including expression of β-actin, desmin, and NCAM.

Spontaneous differentiation of pluripotent stem cells in culture or in teratomas generates cell populations with a highly heterogeneous mixture of phenotypes, representing a spectrum of different cell lineages. For most therapeutic purposes, it is desirable for differentiated cells to be relatively uniform—both in terms of the phenotypes they express, and the types of progeny they can generate.

There is a pressing need for technology to generate more homogeneous differentiated cell populations from pluripotent cells of human origin.

SUMMARY

This invention provides a system for efficient production of primate cells that have differentiated from pluripotent cells into cells of the neural lineage. The precursor and terminally differentiated cells of this invention can be used in a number of important applications, including drug testing and therapy to restore nervous system function.

One aspect of the invention is a population of cells comprising a high proportion of cells having features characteristic of the neural lineage, such as neuronal cells, neuronal precursors, oligodendrocytes, glial cells, and neural precursors capable of giving rise to all such cell types. The cells can be identified based on phenotypic markers, such as A2B5, NCAM, MAP-2, Nestin, β-tubulin III, and others listed later in this disclosure, and by characteristic morphological and functional criteria.

Another aspect of the invention is a method of making populations comprising neural cells from pluripotent cells, such as embryonic stem cells, embryonic germ cells, primary embryonic tissue, or stem cells from fetal or adult tissue that have the capacity of differentiating (or being reprogrammed) into cells with a neural phenotype. The method involves culturing the cells with a combination of soluble factors and environmental conditions that are conducive to outgrowth of neural cells with certain desired properties. The invention includes a strategy for optimizing differentiation protocols for differentiating pluripotent stem cells into neural cells, in which candidate factors are grouped according to function, and the stem cells or their progeny are cultured with factor groups in various combinations. The groups important for producing the desired cell type are identified, and then the individual components of each group are removed one by one to determine the minimal composition required.

By way of illustration, pluripotent stem cells can be produced by direct differentiation on a solid surface in the presence of one or more added TGF-β superfamily antagonists, such as noggin and follistatin. Alternatively, pluripotent stem cells can be cultured as clusters or embryoid bodies. Enrichment for neural cells of varying degrees of maturity comprises culturing in a medium containing added mitogens or growth factors (such as EGF and FGF), concurrently or followed by added neurotrophins (such as NT-3 or BDNF) and other factors (such as EPO) in various optimized combinations. Lists of differentiation factors useful in certain circumstances are listed in the general description and illustrative examples that follow. Optionally, the practitioner may also employ a physical separation technique or manipulation technique that further facilitates enrichment of the cells.

Mature neurons and their precursors prepared according to this invention can be characterized as being progeny of the cell population or an established cell line from which they were derived. This can be demonstrated by showing the genome of the neural cells is essentially the same as that of the parent population, by some suitable technique such as standard DNA fingerprinting. Alternatively, the relationship can be established by review of records kept during derivation of the neural cells. The characteristic that the neural cells are derived from the parent cell population is important in several respects. In particular, the undifferentiated cell population can be used for producing additional cells with a shared genome—either a further batch of neural cells, or another cell type that may be useful in therapy—such as a population that can pretolerize the patient to the histocompatibility type of the neural allograft.

In one embodiment of the invention, neural cells are made from human pluripotent cells differentiated as described into neuronal precursor cells, and then passaged in culture. Using embryonic stem cells as the originating cell type facilitates generation of a rapidly expanding population that nonetheless maintains full capacity to undergo terminal differentiation into functioning neurons—either when cultured with neurotrophins in the absence of mitogens, or when administered to a suitable subject. Depending on the conditions used, precursor populations can be generated that have the capacity to differentiate into a high proportion of tyrosine hydroxylase positive cells. This phenotype is consistent with dopaminergic neurons, desirable for treatment of Parkinson's disease.

The cells of this invention can be used for screening a compound for neural cell toxicity or modulation. A culture is prepared containing the compound and the neural cells, and any phenotypic or metabolic change in the cell that results from contact with the compound is determined. The cells being tested may be dopaminergic, serotonergic, or cholinergic neurons, sensory or motor neurons, oligodendrocytes or astrocytes, or any of the neural precursor cells described in this application. It is often commercially valuable to determine whether the compound is toxic to cells in the population. It may also be valuable to determine it the compound changes neurotransmitter synthesis, release, or uptake by cells in the population, or if the compound changes electrophysiological characteristics of cells in the population.

The cells of this invention can also be used for reconstituting or supplementing the function of the nervous system in an individual, in which the individual is administered with an isolated cell or cell population of this invention. For this purpose, the isolated cells and cell populations are formulated as a medicament for use in treating conditions that affect the nervous system.

These and other embodiments of the invention will be apparent from the description that follows.

DRAWINGS

FIG. 1 shows the growth of cells bearing neural markers that were derived from human embryonic stem cells. The upper panel shows growth of cells maintained in the presence of CNTF, bFGF, and NT3, and then sorted for expression of NCAM. The lower panel shows growth of cells derived from four different ES cell populations maintained in the presence of EGF, bFGF, PDGF, and IGF-1, and then sorted for expression of A2B5. The A2B5 selected population has been passaged over 7 times, and can be further differentiated into both neuronal and glial cells.

FIG. 2 is a fluorescence micrograph showing a cell staining for tyrosine hydroxylase (TH), a marker for dopaminergic cells. Embryoid bodies made from human ES cells were maintained in 10 μm retinoic acid for 4 days, plated into a neural-supportive cocktail, and then passaged into medium containing 10 ng/mL NT-3 and 10 ng/mL BDNF. Certain populations of this invention contain >1% TH-positive cells.

FIG. 3 shows response of the neural-restricted precursors to various neurotransmitters. Panel A shows the ratio of emission data from single cells on two different coverslips. Both cells responded to GABA, elevated potassium, acetylcholine and ATP. Panel B shows the frequency of cells tested that responded to specific neurotransmitters. Panel C shows the combinations of neurotransmitter responses observed.

FIG. 4 shows electrophysiology of neural-restricted precursors. Panel A shows sodium and potassium currents observed in two cells depolarized to test potentials between −80 and 80 mV from a holding potential of −100 mV. Panel B shows the inward ($Na^+$) and outward (K) peak current-voltage relationships observed. Panel C shows action potentials generated by the same cells in response to depolarizing stimuli. These measurements show that neural precursor cells derived from human ES cells are capable of generating action potentials characteristic of neurotransmission.

FIG. 5 is a fluorescence micrograph showing neuronal cells obtained by direct differentiation of ES cells on a solid substrate using a mixture of differentiation factors. The three fields shown were all taken from treatments that comprised neurotrophins and the TNF-β superfamily antagonists noggin and follistatin. A number of cells are seen that have neuronal processes and stain for the neuronal marker β-tubulin-III. The proportion of MAP-2 positive cells that were also positive for tyrosine hydroxylase (a marker for dopaminergic neurons) was as high as ~15%.

FIG. 6 shows aspects of making neurons from hES cells by direct differentiation. Yield of β-tubulin positive neurons is high when undifferentiated cells are plated on laminin and cultured with the TGF-β superfamily antagonists noggin (N) and follistatin (F) (Panel A). Yield was further enhanced in the presence of stem cell factors but not mitogens (Treatment F, Panel B). Retinoic acid increased the number of neurons produced (Panel C), but reduced the proportion of neurons staining positively for tyrosine hydroxylase (TH) (Panel D).

FIG. 7 shows aspects of making neurons in which differentiation was initiated by culturing hES to form embryoid bodies. The cells were then cultured in mitogens, subject to differential trypsinization, and then put through multiple passages in a medium containing a cocktail of mitogens or neurotrophic factors. When both mitogens and neurotrophins were used, the cells could be passaged through about 40 doublings (Panel A), retaining proliferative capacity and the ability to differentiate into mature neurons (Panel B).

FIG. 8 shows that passaging the cells in a mixture of epidermal growth factor (EGF), basic fibroblast growth factor (FGF-2), brain-derived neurotrophic factor (BDNF) and neurotrophin 3 (NT-3) generated populations of neural precursors which upon differentiation produced cell populations that comprised ~7% TH-positive cells, as a percentage of total cells in the population (Panel A). The cocktail used for terminal differentiation of the precursor cells can also improve the production of TH-positive cells (Panel B).

DETAILED DESCRIPTION

It has been discovered that when pluripotent stem cells are cultured in the presence of selected differentiating agents, a population of cells is derived that has a remarkably high proportion of cells with phenotypic characteristics of mature neural cells or their precursors. These cells are suitable for use in drug screening and the therapy of conditions related to abnormalities of the nervous system.

The system encompassed by this invention is illustrated by cell populations obtained from an established line of human embryonic stem (hES) cells. Differentiation can be initiated by forming embryoid bodies, or by culturing the hES cells with TGF-β superfamily antagonists.

Neurons obtained according to this invention have extended processes characteristic of this cell type, show staining for neuron-specific markers like neurofilament and MAP-2, and show evidence of synapse formation, as detected by staining for synaptophysin. FIG. 3 shows that these cells respond to a variety of neurotransmitter substances. FIG. 4 shows that these cells are capable of action potentials as measured in a standard patch-clamp system. In all these respects, the cells are apparently capable of full neurological function.

Neural precursors formed from hES cells can be passaged in culture through about 40 doublings, as shown in FIG. 7(A). Remarkably, even after multiple passages, the cells retain full capacity to differentiate into mature neurons, as shown in FIG. 7(B). This powerful combination of proliferative capacity and differentiation capacity has not previously been available for human neural cells in culture.

Of particular interest is the capacity of this system to be adjusted to optimize the proportion of precursors capable of generating neurons with therapeutically important features. FIGS. 2 and 5 show neurons staining positively for tyrosine hydroxylase, characteristic of dopaminergic neurons. Cells of this type are particularly desirable for the treatment of Parkinson's disease, but no other source described previously can supply the right kind of cells with sufficient abundance. As shown in FIG. 8, passaging precursor cells in a medium containing mitogens EGF and FGF-2, and neurotrophins BDNF and NT-3 generates a proliferating cell population capable of generating ~7% TH-positive cells, as a percentage of total cells in the population.

Since pluripotent stem cells and some of the lineage-restricted precursors of this invention proliferate extensively in culture, the system described in this disclosure provides an unbounded supply of neuronal and glial cells for use in research, pharmaceutical development, and the therapeutic management of CNS abnormalities. The preparation and utilization of the cells of this invention is illustrated further in the description that follows.

Definitions

For the purposes of this disclosure, the terms "neural progenitor cell" or "neural precursor cell" mean a cell that can generate progeny that are either neuronal cells (such as neuronal precursors or mature neurons) or glial cells (such as glial precursors, astrocytes, or oligodendrocytes). Typically, the cells express some of the phenotypic markers that are characteristic of the neural lineage. Typically, they do not produce progeny of other embryonic germ layers when cultured by themselves in vitro, unless dedifferentiated or reprogrammed in some fashion.

A "neuronal progenitor cell" or "neuronal precursor cell" is a cell that can generate progeny that are mature neurons. These cells may or may not also have the capability to generate glial cells. A "glial progenitor cell" or "glial precursor cell" is a cell that can generate progeny that are astrocytes or oligodendrocytes. These cells may or may not also have the capability to generate neuronal cells.

A mature or terminally differentiated neuron is a cell that has neural processes or other morphological features typical of such cells. Cells characterized as neurons will often also be capable of releasing a neurotransmitter, firing an action potential, or making synapses, and can have cell surface markers typical of mature neurons, as illustrated below.

In the context of cell ontogeny, the adjective "differentiated" is a relative term. A "differentiated cell" is a cell that has progressed further down the developmental pathway than the cell it is being compared with. Thus, pluripotent embryonic stem cells can differentiate to lineage-restricted precursor cells, such as the various types of neural progenitors listed above. These in turn can be differentiated further to other types of precursor cells further down the pathway, or to an end-stage differentiated cell, such as neurons, astrocytes, or oligodendrocytes.

A "differentiation agent", as used in this disclosure, refers to one of a collection of compounds that are used in culture systems of this invention to produce differentiated cells of the neural lineage (including precursor cells and terminally differentiated cells). No limitation is intended as to the mode of action of the compound. For example, the agent may assist the differentiation process by inducing or assisting a change in phenotype, promoting growth of cells with a particular phenotype or retarding the growth of others, or acting in concert with other agents through unknown mechanisms.

Prototype "primate Pluripotent Stem cells" (pPS cells) are pluripotent cells derived from pre-embryonic, embryonic, or fetal tissue at any time after fertilization, and have the characteristic of being capable under appropriate conditions of producing progeny of several different cell types that are derivatives of all of the three germinal layers (endoderm, mesoderm, and ectoderm), according to a standard art-accepted test, such as the ability to form a teratoma in 8-12 week old SCID mice. Included in the definition of pPS cells are embryonic cells of various types, exemplified by human embryonic stem (hES) cells, and human embryonic germ (hEG) cells. The pPS cells are preferably not derived from a malignant source. It is desirable (but not always necessary) that the cells be euploid.

pPS cell cultures are described as "undifferentiated" when a substantial proportion of stem cells and their derivatives in the population display morphological characteristics of undifferentiated cells, clearly distinguishing them from differentiated cells of embryo or adult origin. Undifferentiated pPS cells are easily recognized by those skilled in the art, and typically appear in the two dimensions of a microscopic view in colonies of cells with high nuclear/cytoplasmic ratios and prominent nucleoli. It is understood that colonies of undifferentiated cells within the population will often be surrounded by neighboring cells that are differentiated.

"Feeder cells" or "feeders" are terms used to describe cells of one type that are co-cultured with cells of another type, to provide an environment in which the cells of the second type can grow. pPS cell populations are said to be "essentially free" of feeder cells if the cells have been grown through at least one round after splitting in which fresh feeder cells are not added to support the growth of pPS cells. Compositions containing less than 1%, 0.2%, 0.05%, or 0.01% feeder cells are increasingly more preferred.

The term "embryoid bodies" refers to aggregates of differentiated and undifferentiated cells that appear when pPS cells overgrow in monolayer cultures, or are maintained in suspension cultures. Embryoid bodies are a mixture of different cell types, typically from several germ layers, distinguishable by morphological criteria and cell markers detectable by immunocytochemistry.

A "growth environment" is an environment in which cells of interest will proliferate, differentiate, or mature in vitro. Features of the environment include the medium in which the cells are cultured, any growth factors or differentiation-inducing factors that may be present, and a supporting structure (such as a substrate on a solid surface) if present.

A cell is said to be "genetically altered", "transfected", or "genetically transformed" when a polynucleotide has been transferred into the cell by any suitable means of artificial manipulation, or where the cell is a progeny of the originally altered cell that has inherited the polynucleotide. The polynucleotide will often comprise a transcribable sequence encoding a protein of interest, which enables the cell to express the protein at an elevated level. The genetic alteration is said to be "inheritable" if progeny of the altered cell have the same alteration.

General Techniques

For further elaboration of general techniques useful in the practice of this invention, the practitioner can refer to standard textbooks and reviews in cell biology, tissue culture, and embryology. Included are *Properties and uses of Embryonic Stem Cells: Prospects for Application to Human Biology and Gene Therapy* (P. D. Rathjen et al., Reprod. Fertil. Dev. 10:31, 1998); and *Embryonic Stem Cells: Methods and Protocol*, Kursad Turksen, ed., Humana Press, 2002.

For elaboration of nervous system abnormalities, and the characterization of various types of nerve cells, markers, and related soluble factors, the reader is referred to *CNS Regeneration: Basic Science and Clinical Advances*, M. H. Tuszynski & J. H. Kordower, eds., Academic Press, 1999. Care and feeding of neural cells is described in *The Neuron: Cell and Molecular Biology*, $3^{rd}$ Edition, I. B. Levitan & L. K. Kaczmarek, Oxford U. Press, 2001; and *The Neuron in Tissue Culture*, L. W. Haynes Ed., John Wiley & Son Ltd, 1999.

Sources of Stem Cells

This invention can be practiced using stem cells of various types. Particularly suitable for use in this invention are primate pluripotent stem (pPS) cells derived from tissue formed after gestation, such as a blastocyst, or fetal or embryonic tissue taken any time during gestation. Non-limiting examples are primary cultures or established lines of embryonic stem cells or embryonic germ cells, as described below. The techniques of this invention can also be implemented directly with primary embryonic or fetal tissue, deriving neural cells directly from primary embryonic cells without first establishing an undifferentiated cell line.

Embryonic stem cells can be isolated from blastocysts of members of the primate species (U.S. Pat. No. 5,843,780; Thomson et al., Proc. Natl. Acad. Sci. USA 92:7844, 1995). Human embryonic stem (hES) cells can be prepared from human blastocyst cells using the techniques described by Thomson et al. (U.S. Pat. No. 6,200,806; Science 282:1145, 1998; Curr. Top. Dev. Biol. 38:133 ff., 1998) and Reubinoff et al, Nature Biotech. 18:399, 2000. Equivalent cell types to hES cells include their pluripotent derivatives, such as primitive ectoderm-like (EPL) cells, as outlined in WO 01/51610 (Bresagen).

Human Embryonic Germ (hEG) cells can be prepared from primordial germ cells present in human fetal material taken about 8-11 weeks after the last menstrual period. Suitable preparation methods are described in Shamblott et al., Proc. Natl. Acad. Sci. USA 95:13726, 1998 and U.S. Pat. No. 6,090,622.

pPS cells can be propagated continuously in culture, using culture conditions that promote proliferation without promoting differentiation. Exemplary serum-containing ES medium is made with 80% DMEM (such as Knockout DMEM, Gibco), 20% of either defined fetal bovine serum (FBS, Hyclone) or serum replacement (WO 98/30679), 1% non-essential amino acids, 1 mM L-glutamine, and 0.1 mM β-mercaptoethanol. Just before use, human bFGF is added to 4 ng/mL (WO 99/20741, Geron Corp.).

Traditionally, ES cells are cultured on a layer of feeder cells, typically a mixed cell population derived from embryonic or fetal tissue (U.S. Pat. No. 6,200,806). Scientists at Geron have discovered that pPS cells can be maintained in an undifferentiated state even without feeder cells. Feeder free cultures can be supported on an extracellular matrix (such as Matrigel® or laminin), and cultured in a nutrient medium containing factors that support proliferation of the cells without differentiation. Exemplary is conditioned medium obtained by preculturing with cells secreting such factors, such as irradiated primary mouse embryonic fibroblasts (or fibroblast-like cells derived from human embryonic stem cells), supplemented with 8 ng/mL basic FGF both before and after conditioning. Under the microscope, ES cells appear with high nuclear/cytoplasmic ratios, prominent nucleoli, and compact colony formation, typically expressing characteristic phenotypic markers such as SSEA 3 and 4. Further elaboration of the care and feeding of embryonic stem cells is provided in International Patent Publications WO 99/20741 and WO 01/51616.

Some of the techniques described in this invention can also be used to maintain or advance the differentiation of neural cells or neural precursors obtained from fetal or adult tissue. Such cells are outlined in U.S. Pat. Nos. 5,852,832; 5,654,183; 5,849,553; and 5,968,829; and WO 09/50526 and WO 99/01159. Except where otherwise specified, the invention can be practiced using cells of any vertebrate species. Included are stem cells from humans; as well as non-human primates, domestic animals, and other non-human mammals.

Materials and Procedures for Preparing Neural Precursors and Terminally Differentiated Cells The neural progenitors and mature neurons of this invention can be made by differentiating stem cells using a suitable differentiation paradigm.

Typically, differentiation protocols are conducted in a culture environment comprising a suitable substrate, and a nutrient medium to which the differentiation agents are added. Suitable substrates include solid surfaces coated with a positive charge, exemplified by poly-L-lysine and polyornithine. Substrates can be coated with extracellular matrix components, exemplified by fibronectin and laminin. Other permissive extracellular matrixes include Matrigel® (extracellular matrix from Engelbreth-Holm-Swarm tumor cells). Also suitable are combination substrates, such as poly-L-lysine combined with fibronectin, laminin, or both.

Neural lineage cells of this invention are cultured in a medium that supports the proliferation or survival of the desired cell type. It is often desirable to use a defined medium that supplies nutrients as free amino acids rather than serum. It is also beneficial to supplement the medium with additives developed for sustained cultures of neural cells. Exemplary are N2 and B27 additives, available commercially from Gibco.

Advancing cells along the neural differentiation pathway is promoted by including in the culture medium a cocktail of differentiation agents that enhances outgrowth of the desired cell type. This may involve directing the cells or their progeny to adopt phenotypic features of the differentiated cell type, promoting the growth of cells with the desired phenotype, or inhibiting growth of other cell types. It is usually not necessary to understand the mode of action of the agents in order to practice the invention.

Suitable differentiation agents include growth factors of various kinds, such as epidermal growth factor (EGF), transforming growth factor a (TGF-α), any type of fibroblast growth factor (exemplified by FGF-4, FGF-8, and basic fibroblast growth factor=bFGF), platelet-derived growth factor (PDGF), insulin-like growth factor (IGF-1 and others), high concentrations of insulin, sonic hedgehog, members of the neurotrophin family (such as nerve growth factor=NGF, neurotrophin 3=NT-3, brain-derived neurotrophic factor=BDNF), bone morphogenic proteins (especially BMP-2 & BMP-4), retinoic acid (RA) and ligands to receptors that complex with gp130 (such as LIF, CNTF, and IL-6). Also suitable are alternative ligands and antibodies that bind to the respective cell-surface receptors for the aforementioned factors. Typically, a plurality of differentiation agents is used, which may comprise 2, 3, 4, or more of the agents listed above or in the examples below.

In one differentiation method, pPS cells are plated directly onto a suitable substrate, such as an adherent glass or plastic surface, such as coverslips coated with poly-lysine, with or without a neuron-friendly matrix protein such as fibronectin or laminin. The cells are then cultured in a suitable nutrient medium that is adapted to promote differentiation towards neural cells. This is referred to as the "direct differentiation" method, which is further illustrated in International Patent Publication WO 01/51616, and priority U.S. patent application Ser. No. 09/888,309. TGF-β superfamily antagonists such as noggin and follistatin are especially useful in directing neural differentiation and enhancing the proportion of cells bearing phenotypic features of neural cells obtained by direct differentiation (Example 9).

In another differentiation method, pPS cells are first pre-differentiated into a heterogeneous cell population by forming cell clusters. In an exemplary variation, embryoid bodies are formed from the pPS cells by culturing them in suspension. Optionally, one or more of the differentiation agents listed earlier (such as retinoic acid) can be included in the medium to promote differentiation within the embryoid body. After the embryoid bodies have reached sufficient size or maturity (typically 3-4 days), they are plated onto the substrate of the differentiation culture. The embryoid bodies can be plated directly onto the substrate without dispersing the cells. This allows neural cell precursors to migrate out of the embryoid bodies and on to the extracellular matrix. In some procedures, the cells are first cultured in a mitogen cocktail, such as EGF, bFGF, PDGF, and IGF-1, and then passaged in a combination of mitogens and neurotrophins to select out neural progenitor cells.

This invention includes a strategy for identifying factor combinations effective for generating particular neural phenotypes. Various factors known or suspected to enhance neural differentiation or growth are categorized into various functional classes, based on known effects on neural cells from other tissues or species, known receptor binding activities, structural homology with other factors of known function, or other appropriate criteria. Factors within each class are pooled at a suitable working concentration. Cells are then cultured with each of the factor classes together, in various combinations, and the factors are assessed on the ability to promote growth of precursor cells or mature neurons of the desired type. Essential factor classes are identified when their absence causes the mixture to lose its ability to promote the desired phenotype. Once essential classes are identified and others are eliminated, then each of the classes is dissected by removing single components until the minimal cocktail is identified. The implementation of this strategy is illustrated in Example 9.

If desired, the differentiated cells can be sorted to enrich for certain populations. For example, the cells can be contacted with an antibody or ligand that binds to a marker characteristic of neural cells (such as NCAM), followed by separation of the specifically recognized cells using a suitable immunological technique, such as solid phase adsorption or fluorescence-activated cell sorting. Also suitable are differential plating or harvesting techniques, in which adherence or releasability of the desired cell type is used to separate it from other cells in a heterogeneous population.

It has been discovered that neural precursor phenotype can be passaged in proliferating culture using a combination of mitogens (such as bFGF and EGF), plus one or more neurotrophins (such as BDNF, NT-3, or both). This is illustrated in Examples 6, 9 and 10. The cells can be passaged for up to 40 doublings according to this method (FIG. 7), while retaining both an ability to proliferate and an ability to make mature neurons.

It is hypothesized that committed progenitor cells will have particular value in human therapy, because they are more resilient to manipulation, and will retain a greater ability to migrate to the target tissue and integrate in a functionally compatible fashion. Progenitor cells can be grown either on a solid surface as illustrated in Example 10, or in suspension culture, where they tend to form clusters or spherical structures. By way of illustration, neural progenitors are harvested using trypsin when nearly confluent. They are then seeded at about half density in nonadherent wells, and cultured in supplemented medium containing 10 ng/mL of BDNF, NT-3, EGF, and bFGF, changed about 3 times per week.

Judicious selection of other components of the culture medium during derivation or maintenance of the neural progenitor cells can influence the range and character of mature cells that they can generate. As illustrated in Example 9, including retinoic acid in the medium during direct differentiation of neural progenitors increases the proportion of MAP-2 cells produced upon terminal differentiation—but decreases the proportion of cells positive for tyrosine hydroxylase (TH), which correlates with dopaminergic neurons. On the other hand, it has been discovered that including erythropoietin (EPO) or agents that increase cyclic AMP levels in the culture medium during neural progenitor formation enhances the capacity for forming TH positive neurons. As an alternative, cells can be cultured with certain antibodies or agonists that activate the EPO pathway, or the cells can be cultured under mildly hypoxic conditions (low $O_2$ levels, say 3-6%). Use of EPO to enhance formation of the dopaminergic phenotype is illustrated in Example 7.

Neural precursor cells prepared according to any of these procedures can be further differentiated to mature neurons. Fully differentiated cells are desirable for various applications of this invention, such as the in vitro assessment and screening of various compounds for their effect on neural tissue. It is also useful to make fully differentiated cells to characterize the functional capabilities of neural progenitors from which they came.

Differentiated neurons can be formed by culturing precursor cells with a maturation factor, such as forskolin (or other compound that elevates intracellular cAMP levels such as cholera toxin, isobutylmethylxanthine, dibutyladenosine cyclic monophosphate), c-kit ligand, retinoic acid, or any factor or combination of factors from the family of neurotrophins. Particularly effective are neurotrophin-3 (NT-3) in combination with brain-derived neurotrophic factor (BDNF). Other candidates are GDNF, BMP-2, and BMP-4. Alternatively or in addition, maturation can be enhanced by withdrawing some or all of the factors that promote neural precursor proliferation, such as EGF, FGF, or other mitogens previously used to maintain the culture.

Further Manipulation

Many of the neural cell precursor populations of this invention have a substantial proliferation capacity. If desired, the replication capacity can be further enhanced by increasing the level of telomerase reverse transcriptase (TERT) in the cell, either by increasing transcription from the endogenous gene, or by introducing a transgene. Particularly suitable is the catalytic component of human telomerase (hTERT), provided in International Patent Application WO 98/14592. Transfection and expression of telomerase in human cells is described in Bodnar et al., Science 279:349, 1998 and Jiang et al., Nat. Genet. 21:111, 1999. Genetically altered cells can be assessed for hTERT expression by RT-PCR, telomerase activity (TRAP assay), immunocytochemical staining for hTERT, or replicative capacity, according to standard methods.

For use in therapeutic and other applications, it is often desirable that populations of precursor or mature neurological cells be substantially free of undifferentiated pPS cells. One way of depleting undifferentiated stem cells from the population is to transfect them with a vector in which an effector gene under control of a promoter that causes preferential expression in undifferentiated cells. Suitable promoters include the TERT promoter and the OCT-4 promoter. The effector gene may be directly lytic to the cell (encoding, for example, a toxin or a mediator of apoptosis). Alternatively, the effector gene may render the cell susceptible to toxic effects of an external agent, such as an antibody or a prodrug. Exemplary is a herpes simplex thymidine kinase (tk) gene, which causes cells in which it is expressed to be susceptible to ganciclovir. Suitable pTERT-tk constructs are provided in International Patent Publication WO 98/14593 (Morin et al.).

Characteristics of Neural Precursors and Terminally Differentiated Cells

Cells can be characterized according to a number of phenotypic criteria, such as morphological features, detection or quantitation of expressed cell markers, enzymatic activity, or neurotransmitters and their receptors, and electrophysiological function.

Certain cells embodied in this invention have morphological features characteristic of neuronal cells or glial cells. The features are readily appreciated by those skilled in evaluating the presence of such cells. For example, characteristic of neurons are small cell bodies, and multiple processes reminiscent of axons and dendrites. Cells of this invention can also be characterized according to whether they express phenotypic markers characteristic of neural cells of various kinds.

Markers of interest include but are not limited to β-tubulin III, microtubule-associated protein 2 (MAP-2), or neurofilament, characteristic of neurons; glial fibrillary acidic protein (GFAP), present in astrocytes; galactocerebroside (GalC) or myelin basic protein (MBP), characteristic of oligodendrocytes; Oct-4, characteristic of undifferentiated hES cells; and Nestin, characteristic of neural precursors and other cells. Both A2B5 (a glycolipid) and polysialylated Neural Cell Adhesion Molecule (abbreviated NCAM) have already been described. While A2B5 and NCAM are instructive markers when studying neural lineage cells, it should be appreciated that these markers can sometimes be displayed on other cell types, such as liver or muscle cells. β-Tubulin III was previously thought to be specific for neural cells, but it has been discovered that a subpopulation of hES cells is also β-tubulin III positive. MAP-2 is a more stringent marker for fully differentiated neurons of various types. Certain cell populations prepared according to this invention comprise at least 30%, 50%, 75%, 90% or more that test positive for these markers, either alone or in various combinations.

Tissue-specific markers listed in this disclosure and known in the art can be detected using any suitable immunological technique—such as flow immunocytochemistry for cell-surface markers, immunohistochemistry (for example, of fixed cells or tissue sections) for intracellular or cell-surface markers, Western blot analysis of cellular extracts, and enzyme-linked immunoassay, for cellular extracts or products secreted into the medium. Expression of an antigen by a cell is said to be "antibody-detectable" if a significantly detectable amount of antibody will bind to the antigen in a standard immunocytochemistry or flow cytometry assay, optionally after fixation of the cells, and optionally using a labeled secondary antibody or other conjugate (such as a biotin-avidin conjugate) to amplify labeling.

The expression of tissue-specific gene products can also be detected at the mRNA level by Northern blot analysis, dot-blot hybridization analysis, or by reverse transcriptase initiated polymerase chain reaction (RT-PCR) using sequence-specific primers in standard amplification methods. See U.S. Pat. No. 5,843,780 for further details. Sequence data for the particular markers listed in this disclosure can be obtained from public databases such as GenBank. Expression at the mRNA level is said to be "detectable" according to one of the assays described in this disclosure if the performance of the assay on cell samples according to standard procedures in a typical controlled experiment results in clearly discernable hybridization or amplification product. Expression of tissue-specific markers as detected at the protein or mRNA level is considered positive if the level is at least 2-fold, and preferably more than 10- or 50-fold above that of a control cell, such as an undifferentiated pPS cell, a fibroblast, or other unrelated cell type.

Also characteristic of neural cells, particularly terminally differentiated cells, are receptors and enzymes involved in the biosynthesis, release, and reuptake of neurotransmitters, and ion channels involved in the depolarization and repolarization events that relate to synaptic transmission. Evidence of synapse formation can be obtained by staining for synaptophysin. Evidence for receptivity to certain neurotransmitters can be obtained by detecting receptors for γ-amino butyric acid (GABA), glutamate, dopamine, 3,4-dihydroxyphenylalanine (DOPA), noradrenaline, acetylcholine, and serotonin.

Differentiation of particular neural precursor cell populations of this invention (for example, using NT-3 and BDNF) can generate cell populations that are at least 20%, 30%, or 40% MAP-2 positive. A substantial proportion, say 5%, 10%, 25%, or more of the NCAM or MAP-2 positive cells (on a cell count basis) will be capable of synthesizing a neurotransmitter, such as acetylcholine, glycine, glutamate, norepinephrine, serotonin, or GABA. Certain populations of the invention contain NCAM or MAP-2 positive cells that have 1%, 5%, 10% or more that are positive for tyrosine hydroxylase (TH), measured by immunocytochemistry or mRNA expression—either as a percentage of NCAM or MAP-2 positive cells, or all cells present in the population. TH is generally considered in the art to be a marker for dopamine synthesizing cells.

To elucidate further mature neurons present in a differentiated population, the cells can be tested according to functional criteria. For example, calcium flux can be measured by any standard technique, in response to a neurotransmitter, or other environmental condition known to affect neurons in vivo. First, neuron-like cells in the population are identified by morphological criteria, or by a marker such as NCAM. The neurotransmitter or condition is then applied to the cell, and the response is monitored (Example 6). The cells can also be subjected to standard patch-clamp techniques, to determine whether there is evidence for an action potential, and what the lag time is between applied potential and response.

Where derived from an established line of pPS cells, the cell populations and isolated cells of this invention can be characterized as having the same genome as the line from which they are derived. This means that the chromosomal DNA will be over 90% identical between the pPS cells and the neural cells, which can be inferred if the neural cells are obtained from the undifferentiated line through the course of normal mitotic division. Neural cells that have been treated by recombinant methods to introduce a transgene (such as TERT) or knock out an endogenous gene are still considered to have the same genome as the line from which they are derived, since all non-manipulated genetic elements are preserved.

Use of Neural Precursors and Terminally Differentiated Cells

This invention provides a method to produce large numbers of neural precursor cells and mature neuronal and glial cells. These cell populations can be used for important research, development, and commercial purposes.

The cells of this invention can be used to prepare a cDNA library relatively uncontaminated with cDNA preferentially expressed in cells from other lineages. For example, multipotent neural progenitor cells are collected by centrifugation at 1000 rpm for 5 min, and then mRNA is prepared, reverse transcribed, and optionally subtracted with cDNA from mature neurons, astrocytes, or oligodendrocytes, or undifferentiated astrocytes. Expression patterns of neurons can be compared with other cell types by microarray analysis, reviewed generally by Fritz et al Science 288:316, 2000; "Microarray Biochip Technology", L Shi.

The differentiated cells of this invention can also be used to prepare antibodies that are specific for markers of multipotent neural progenitors, cells committed to the neuronal or glial cell lineage, and mature neurons, astrocytes, and oligodendrocytes. Polyclonal antibodies can be prepared by injecting a vertebrate animal with cells of this invention in an immunogenic form. Production of monoclonal antibodies is described in such standard references as Harrow & Lane (1988), U.S. Pat. Nos. 4,491,632, 4,472,500 and 4,444,887, and *Methods in Enzymology* 73B:3 (1981).

Applications of commercial interest include the use of cells to screen small molecule drugs, and the preparation of pharmaceutical compositions comprising neurons for clinical therapy.

Drug Screening

Neural precursor cells of this invention can be used to screen for factors (such as solvents, small molecule drugs, peptides, polynucleotides) or environmental conditions (such as culture conditions or manipulation) that affect the characteristics of neural precursor cells and their various progeny.

In some applications, pPS cells (undifferentiated or differentiated) are used to screen factors that promote maturation into neural cells, or promote proliferation and maintenance of such cells in long-term culture. For example, candidate maturation factors or growth factors are tested by adding them to cells in different wells, and then determining any phenotypic change that results, according to desirable criteria for further culture and use of the cells.

Other screening applications of this invention relate to the testing of pharmaceutical compounds for their effect on neural tissue or nerve transmission. Screening may be done either because the compound is designed to have a pharmacological effect on neural cells, or because a compound designed to have effects elsewhere may have unintended side effects on the nervous system. The screening can be conducted using any of the neural precursor cells or terminally differentiated cells of the invention, such as dopaminergic, serotonergic, cholinergic, sensory, and motor neurons, oligodendrocytes, and astrocytes.

The reader is referred generally to the standard textbook "in vitro Methods in Pharmaceutical Research", Academic Press, 1997, and U.S. Pat. No. 5,030,015. Assessment of the activity of candidate pharmaceutical compounds generally involves combining the differentiated cells of this invention with the candidate compound, either alone or in combination with other drugs. The investigator determines any change in the morphology, marker phenotype, or functional activity of the cells that is attributable to the compound (compared with untreated cells or cells treated with an inert compound), and then correlates the effect of the compound with the observed change.

Cytotoxicity can be determined in the first instance by the effect on cell viability, survival, morphology, and the expression of certain markers and receptors. Effects of a drug on chromosomal DNA can be determined by measuring DNA synthesis or repair. [$^3$H]-thymidine or BrdU incorporation, especially at unscheduled times in the cell cycle, or above the level required for cell replication, is consistent with a drug effect. Unwanted effects can also include unusual rates of sister chromatid exchange, determined by metaphase spread. The reader is referred to A. Vickers (pp 375-410 in "In vitro Methods in Pharmaceutical Research," Academic Press, 1997) for further elaboration.

Effect of cell function can be assessed using any standard assay to observe phenotype or activity of neural cells, such as receptor binding, neurotransmitter synthesis, release or uptake, electrophysiology, and the growing of neuronal processes or myelin sheaths—either in cell culture or in an appropriate model. For example, the ability of drugs to alter synaptic contact and plasticity can be measured in culture by immunocytochemical staining for synapsin or synaptophysin. Electrophysiology can be assessed by measuring measure IPSPs and EPSPs (inhibitory and excitatory postsynaptic potentials). Alternatively, using a two electrode system, one cell is stimulated, and the response of a second cell in the system is evaluated. The behavior of the system in the presence of the candidate drug is compared with the behavior in the absence of the drug, and correlated with an ability of the drug to affect synaptic contact or cell plasticity.

Therapeutic Use

This invention also provides for the use of neural precursor cells to restore a degree of central nervous system (CNS) function to a subject needing such therapy, perhaps due to an inborn error in function, the effect of a disease condition, or the result of an injury.

To determine the suitability of neural precursor cells for therapeutic administration, the cells can first be tested in a suitable animal model. At one level, cells are assessed for their ability to survive and maintain their phenotype in vivo. Neural precursor cells are administered to immunodeficient animals (such as nude mice, or animals rendered immunodeficient chemically or by irradiation) at an observable site, such as in the cerebral cavity or in the spinal cord. Tissues are harvested after a period of a few days to several weeks or more, and assessed as to whether pPS derived cells are still present.

This can be performed by administering cells that express a detectable label (such as green fluorescent protein, or β-galactosidase); that have been prelabeled (for example, with BrdU or [$^3$H]thymidine), or by subsequent detection of a constitutive cell marker (for example, using human-specific antibody). Where neural precursor cells are being tested in a rodent model, the presence and phenotype of the administered cells can be assessed by immunohistochemistry or ELISA using human-specific antibody, or by RT-PCR analysis using primers and hybridization conditions that cause amplification to be specific for human polynucleotide sequences. Suitable markers for assessing gene expression at the mRNA or protein level are provided elsewhere in this disclosure.

Various animal models for testing restoration of nervous system function are described in "*CNS Regeneration: Basic Science and Clinical Advances*", M. H. Tuszynski & J. H. Kordower, eds., Academic Press, 1999.

Differentiated cells of this invention can also be used for tissue reconstitution or regeneration in a human patient in need thereof. The cells are administered in a manner that permits them to graft or migrate to the intended tissue site and reconstitute or regenerate the functionally deficient area. Certain neural progenitor cells embodied in this invention are designed for treatment of acute or chronic damage to the nervous system. For example, excitotoxicity has been implicated in a variety of conditions including epilepsy, stroke, ischemia, and Alzheimer's disease. Dopaminergic neurons may be formulated for treating Parkinson's disease, GABAergic neurons for Huntington's disease, and motor neurons for spinal cord injury or amyotrophic lateral sclerosis (ALS). Cell populations enriched in oligodendrocytes or oligodendrocyte precursors to promote remyelination may be formulated for treating spinal cord injuries, and myelination disorders such as Pelizaeus-Merzbacher disease, multiple sclerosis, adenoleukodystrophies, neuritis and neuropathies.

By way of illustration, neural stem cells are transplanted directly into parenchymal or intrathecal sites of the central nervous system, according to the disease being treated. Grafts are done using single cell suspension or small aggregates at a density of 25,000-500,000 cells per µL (U.S. Pat. No. 5,968,829). The efficacy of transplants of motor neurons or their precursors can be assessed in a rat model for acutely injured spinal cord as described by McDonald et al. (Nat. Med. 5:1410, 1999). A successful transplant will show transplant-derived cells present in the lesion several weeks later, differentiated into astrocytes, oligodendrocytes, and/or neurons, and migrating along the cord from the lesioned end, and an improvement in gate, coordination, and weight-bearing.

The neural progenitor cells and terminally differentiated cells according to this invention can be supplied in the form of a pharmaceutical composition, comprising an isotonic excipient prepared under sufficiently sterile conditions for human administration. For general principles in medicinal formulation, the reader is referred to *Cell Therapy: Stem Cell Transplantation, Gene Therapy, and Cellular Immunotherapy*, by G. Morstyn & W. Sheridan eds, Cambridge University Press, 1996; and *Hematopoietic Stem Cell Therapy*, E. D. Ball, J. Lister & P. Law, Churchill Livingstone, 2000.

The composition may optionally be packaged in a suitable container with written instructions for a desired purpose, such as the reconstitution of CNS function to improve some neurological abnormality.

The following examples are provided as further non-limiting illustrations of particular embodiments of the invention.

EXAMPLES

Example 1

NCAM-positive Cells

This experiment focused on determining whether the human embryonic stem cells (hES) could undergo directed differentiation to NCAM-positive progenitor cells.

hES cells were harvested either from cultures supported by embryonic fibroblasts, or from feeder-free cultures, as described previously (AU 729377; WO 01/51616). Embryoid bodies were produced as follows. Confluent monolayer cultures of hES cells were harvested by incubating in 1 mg/mL collagenase for 5-20 min, following which the cells are scraped from the plate. The cells were then dissociated into clusters and plated in non-adherent cell culture plates (Costar) in a medium composed of 80% KO ("knockout") DMEM (Gibco) and 20% non-heat-inactivated FBS (Hyclone), supplemented with 1% non-essential amino acids, 1 mM glutamine, 0.1 mM β-mercaptoethanol. The cells are seeded at a 1:1 or 1:2 ratio in 2 mL medium per well (6 well plate).

After 4-8 days in suspension, the EBs were plated intact in DMEM/F12 medium containing B27 supplement (Gibco), N2 supplement (Gibco), and 25 ng/mL human bFGF. Wells were coated with fibronectin (Sigma) at a final concentration of 20 μg/mL in PBS. After culturing for about 2-3 days, NCAM-positive cells and A2B5-positive cells were identified by immunostaining.

Magnetic bead sorting and immunopanning were both successful in enriching NCAM-positive cells. The starting population of cells typically contained 25-72% NCAM-positive cells. After immuno-isolation, the NCAM-positive proportion was enriched to 43-72%. Results are shown in Table 1.

TABLE 1

Differentiation and Sorting Conditions for NCAM positive Cells

| hES Cell Line used for Differentiation | Factors used in Differentiation Culture | Type of Sort | Before sort | Positive sort | Negative sort |
|---|---|---|---|---|---|
| H13 p28 | C F N | bead sort | 33 | 92 | 41 |
| H13 p28 | C F N | panning | 25 | n/a | n/a |
| H9 p32 | C F N | panning | 64 | 72 | 51 |
| H1 p32 | C F N | bead sort | 27 | 77 | 9 |
| H9 p19 | C F N | bead sort | 58 | 76 | 32 |
| H9 p31 545.184 | C F N | bead sort | 50 | 91 | 67 |
| H1 p40 545.185 | C F N | bead sort A | 65 | 89 | 31 |
| H1 p40 545.185 | C F N | bead sort B | 63 | 81 | 33 |
| H7NG p28/4 545.187 | C F N | bead sort A | 53 | 92 | 45 |
| H7NG p28/4 545.187 | C F N | bead sort B | 72 | 87 | 50 |
| H1 p39 545.189 | C F N I P | bead sort | 16 | 43 | 6 |
| H7 p32 667.004 | C F N I P | bead sort | 25 | 73 | 10 |
| H1 p43 667.010 | C F N I P | bead sort | 47 | 86 | 31 |
| H1 p44 667.012 | C F N I P | bead sort | 52 | 89 | 34 |
| H1 p46 667.020 | E P F I | bead sort | 60 | 23 | 8 |
| H1 p47 667.031 | EPFI - EPFI | bead sort | 53 | 91 | 27 |
| H1 p47 667.033 | CFN - F | bead sort | 41 | 76 | 24 |
| H9 p40MG 667.038 | E P F I | bead sort | 55 | 80 | 25 |

Factor abbreviations:
C—ciliary neurotrophic factor (CNTF)
F—basic fibroblast growth factor (bFGF)
N—neurotrophin 3 (NT3)
I—insulin-like growth factor (IGF-1)
P—platelet-derived growth factor (PDGF)
T—thyroid hormone $T_3$
Ra—retinoic acid
Fk—Forskolin In the first 10 experiments shown, NCAM positive cells retrieved from the sort were plated on poly-L-lysine/laminin in DMEM/F12 with N2 and B27 supplements and 2 mg/mL BSA, 10 ng/mL human CNTF, 10 ng/mL human bFGF and 1 to 10 ng/mL human NT-3. In subsequent experiments, cells were maintained in DMEM/F12 with N2 and B27 supplements and 10 ng/mL EGF, 10 ng/mL bFGF, 1 ng/mL PDGF-AA, and 1 ng/mL IGF-1.

FIG. 1 (Upper Panel) shows the growth curves for the NCAM positive cells. The cells studied in this experiment were prepared by forming embryoid bodies in 20% FBS for 4 days in suspension, then plating onto a fibronectin matrix in DMEM/F12 with N2 and B27 supplements and 25 ng/mL bFGF for 2-3 days. The cells were then positively sorted for NCAM expression, and maintained in a medium containing CNTF, bFGF, and NT3. The sorted cells did not show increased survival relative to the unsorted population. It was found that some of the NCAM positive cells also express β-tubulin III, indicating that these cells have the capacity to form neurons. They also had morphology characteristic of neuronal cells. There were also A2B5 positive cells within this population, which may represent glial progenitor cells. However, very few cells were positive for GFAP, a marker for astrocytes. Although this cell population proliferated in culture, the proportion of NCAM positive cells (and the capacity to form neurons) diminished after several passages.

Example 2

A2B5-positive Cells

Cells in this experiment were immunoselected for the surface marker A2B5. hES cells were induced to form EBs in 20% FBS. After 4 days in suspension, the EBs were plated onto fibronectin in DMEM/F12 with N2 and B27 supplemented with 10 ng/mL human EGF, 10 ng/mL human bFGF, 1 ng/mL human IGF-I, and 1 ng/mL human PDGF-AA. After 2-3 days in these conditions, 25-66% of the cells express A2B5. This population is enriched by magnetic bead sorting to 48-93% purity (Table 2).

TABLE 2

Differentiation and Sorting Conditions for A2B5-positive Cells

| hES Cell Line used for Differentiation | Factors used in Differentiation Culture | Type of Sort | Cells staining positively for A2B5 | | |
|---|---|---|---|---|---|
| | | | Before sort | Positive sort | Negative sort |
| H7 p32 667.004 | C F N I P | bead sort | 25 | 77 | 10 |
| H1 p43 667.010 | C F N I P | bead sort | 62 | n/a | 50 |
| H1 p44 667.012 | C F N I P | bead sort | 56 | 89 | 32 |
| H1 p46 667.020 | E P F I | bead sort | 27 | 48 | 2 |
| H1 p47 667.032 | E P F I | bead sort | 57 | 93 | 30 |
| H9 p40MG 667.038 | E P F I | bead sort | 66 | 93 | 41 |
| H9 p42 667.041 | E P F I | bead sort | 27 | 70 | 6 |

Factor abbreviations:
C—ciliary neurotrophic factor (CNTF)
F—basic fibroblast growth factor (bFGF)
N—neurotrophin 3 (NT3)
I—insulin-like growth factor (IGF-1)
P—platelet-derived growth factor (PDGF)
T—thyroid hormone $T_3$
Ra—retinoic acid
Fk—Forskolin FIG. 1 (Lower Panel) shows the growth curves for the sorted A2B5-positive cells. Four different hES cell populations were used for this study: H1, H7, H9, and H13 (which may be a mixture of two different lines). The cells were maintained in the same media formulation on poly-l-lysine coated plates. The cells proliferate when serially passaged.

A2B5-positive cells were induced to differentiate by the addition of forskolin. These cells have been assessed through different culture passages, as shown in Table 3.

TABLE 3

Phenotypic Features of Mature Neural Cells

| No. of passages after A2B5 sort | Method of Maturation | Neuron-like morphology visible | β-tubulin | GFAP | GalC | A2B5 | NCAM |
|---|---|---|---|---|---|---|---|
| | | | | Cells Staining Positively for: | | | |
| 1 | PICNT + Fk 4 days | yes | 38 ± 9% | | 13 ± 7% | 79 ± 3% | 28 ± 6% |
| 3 | PICNT + Fk 2 days | yes | +++ | | + | +++++ | ++ |
| 7 | +/−EF +/−serum | yes | + | + | ++ | +++ | − |

Factor abbreviations:
C—ciliary neurotrophic factor (CNTF)
F—basic fibroblast growth factor (bFGF)
N—neurotrophin 3 (NT3)
I—insulin-like growth factor (IGF-1)
P—platelet-derived growth factor (PDGF)
T—thyroid hormone $T_3$
Ra—retinoic acid
Fk—Forskolin Even though the cells were sorted for A2B5 expression, the population demonstrated the capacity to generate not only oligodendrocytes, and astrocytes, but also a large proportion of neurons. This is surprising: it was previously thought that A2B5 expressing cells were glial precursors, and would give rise to oligodendrocytes, and astrocytes—while NCAM expressing cells were neuronal precursors, giving rise to mature neurons. This experiment demonstrates that pPS cells can be differentiated into a cell population that proliferates repeatedly in culture, and is capable of generating neurons and glia.

Example 3

Differentiation to Mature Neurons

To generate terminally differentiated neurons, the first stage of differentiation was induced by forming embryoid bodies in FBS medium with or without 10 μM retinoic acid (RA). After 4 days in suspension, embryoid bodies were plated onto fibronectin-coated plates in defined medium supplemented with 10 ng/mL human EGF, 10 ng/mL human bFGF, 1 ng/mL human PDGF-AA, and 1 ng/mL human IGF-1. The embryoid bodies adhered to the plates, and cells began to migrate onto the plastic, forming a monolayer.

After 3 days, many cells with neuronal morphology were observed. The neural precursors were identified as cells positive for BrdU incorporation, nestin staining, and the absence of lineage specific differentiation markers. Putative neuronal and glial progenitor cells were identified as positive for polysialylated NCAM and A2B5. Forty one to sixty percent of the cells expressed NCAM, and 20-66% expressed A2B5, as measured by flow cytometry. A subpopulation of the NCAM-positive cells was found to express β-tubulin III and MAP-2. There was no co-localization with glial markers such as GFAP or GalC. The A2B5 positive cells appeared to generate both neurons and glia. A subpopulation of the A2B5 cells expressed β-tubulin III or MAP-2, and a separate subpopulation expressed GFAP. Some of the cells with neuronal morphology double-stained for both A2B5 and NCAM. Both the NCAM positive and A2B5 positive populations contained far more neurons than glia.

The cell populations were further differentiated by replating the cells in a medium containing none of the mitogens, but containing 10 ng/mL Neurotrophin-3 (NT-3) and 10 ng/mL brain-derived neurotrophic factor (BDNF). Neurons with extensive processes were seen after about 7 days. Cultures derived from embryoid bodies maintained in retinoic acid (RA) showed more MAP-2 positive cells (~26%) than those maintained without RA (~5%). GFAP positive cells were seen in patches. GalC positive cells were identified, but the cells were large and flat rather than having complex processes.

A summary of cell types and markers expressed at different stages of differentiation is provided in Table 4.

TABLE 4

Phenotypic Markers (Immunocytochemistry)

| Undifferentiated hES colonies | NCAM-positive progenitors | A2B5 positive progenitors |
|---|---|---|
| Tra-1-60 + | Nestin subset | Nestin subset |
| Tra-1-81 + | A2B5 subset | NCAM subset |
| SSEA-4 + | β-tubulin III subset | β-tubulin III subset |
| β-tubulin III + + | Map-2 subset | Map-2 subset |
| Nestin − | GFAP − | GFAP rare |
| Map-2 − | GalC − | GalC − |
| Neurofilament (NF) − | AFP − | AFP − |
| GFAP − | muscle-specific actin − | muscle-specific actin − |
| GalC − | | |
| α-fetoprotein − | | |

TABLE 4-continued

Phenotypic Markers (Immunocytochemistry)

muscle-specific actin −
NCAM −
A2B5 −

| Neurons | | Astrocytes | Oligodendrocytes |
|---|---|---|---|
| β-tubulin III | + | GFAP + | GalC + |
| MAP-2 | + | | |
| Neurofilament (NF) | subset | | |
| GABA | subset | | |
| tyrosine hydroxylase | subset | | |
| glutamate | subset | | |
| glycine | subset | | |

The presence of neurotransmitters was also assessed. GABA-immunoreactive cells were identified that co-expressed β-tubulin III or MAP2, and had morphology characteristic of neuronal cells. Occasional GABA-positive cells were identified that did not co-express neuronal markers, but had an astrocyte-like morphology. Neuronal cells were identified that expressed both tyrosine hydroxylase (TH) and MAP-2. Synapse formation was identified by staining with synaptophysin antibody.

FIG. 2 shows TH staining in cultures differentiated from the H9 line of human ES cells. Embryoid bodies were maintained in 10 μM retinoic acid for 4 days, then plated onto fibronectin coated plates in EGF, basic FGF, PDGF and IGF for 3 days. They were next passaged onto laminin in N2 medium supplemented with 10 ng/mL NT-3 and 10 ng/mL BDNF, and allowed to differentiate further for 14 days. The differentiated cells were fixed with 4% paraformaldehyde for 20 min at room temperature, and then developed using antibody to TH, a marker for dopaminergic cells.

Example 4

Calcium Imaging

Standard fura-2 imaging of calcium flux was used to investigate the functional properties of the hES cell derived neurons. Neurotransmitters studied included GABA, glutamate (E), glycine (G), elevated potassium (50 mM $K^+$ instead of 5 mM $K^+$), ascorbic acid (control), dopamine, acetylcholine (ACh) and norepinephrine. The solutions contained 0.5 mM of the neurotransmitter (except ATP at 10 μM) in rat Ringers (RR) solution: 140 mM NaCl, 3 mM KCl, 1 mM $MgCl_2$, 2 mM $CaCl_2$, 10 mM HEPES buffer, and 10 mM glucose. External solutions were set to pH 7.4 using NaOH. Cells were perfused in the recording chamber at 1.2-1.8 mL/min, and solutions were applied by bath application using a 0.2 mL loop injector located ~0.2 mL upstream of the bath import. Transient rises in calcium were considered to be a response if the calcium levels rose above 10% of the baseline value within 60 sec of application, and returned to baseline within 1-2 min.

FIG. 3 shows the response of neural-restricted precursors to various neurotransmitters. Panel A shows the ratio of emission data from single cells on two different coverslips. Addition of the neurotransmitters is indicated above by labeled triangles.

Panel B shows the frequency of cells tested that responded to specific neurotransmitters. Panel C shows the combinations of neurotransmitter responses observed. Of the 53 cells tested, 26 responded to GABA, acetylcholine, ATP and elevated potassium. Smaller subsets of the population responded to other combinations of agonists. Only 2 of the cells failed to respond to any of the agonists applied.

Example 5

Electrophysiology

Standard whole-cell patch-clamp technique was conducted on the hES cell derived neurons, to record ionic currents generated in voltage-clamp mode and the action potential generated in current-clamp mode. The external bath solution was rat Ringers solution (Example 6). The internal solution was 75 mM potassium-aspartate, 50 mM KF, 15 mM NaCl, 11 mM EGTA, and 10 mM HEPES buffer, set to pH 7.2 using KOH.

All 6 cells tested expressed sodium and potassium currents, and fired action potentials. Passive membrane properties were determined with voltage steps from −70 to −80 mV; and produced the following data: average capacitance ($C_m$)=8.97±1.17 pF; membrane resistance ($R_m$)=487.8±42.0 MΩ; access resistance ($R_a$)=23.4±3.62 MΩ. Ionic currents were determined by holding the cells at −100 mV, and stepping to test voltages between −80 and 80 mV in 10 mV increments, producing the following data: average sodium current $I_{Na}$=−531.8±136.4 pA; average potassium current $I_K$=441.7±113.1 pA; $I_{Na}$(density) =−57.7±7.78 pA/pF; $I_K$(density)=48.2±10.4 pA/pF.

FIG. 4 shows results from a typical experiment. Panel A shows sodium and potassium currents observed in two cells depolarized to test potentials between −80 and 80 mV from a holding potential of −100 mV. Panel B shows the inward ($Na^+$) and outward ($K^+$) peak current-voltage relationships observed. Sodium current activates between −30 and 0 mV, reaching a peak at −10 or 0 mV. Potassium current activates above −10 mV, becoming equal or larger in magnitude than the sodium current at voltages between 20 and 40 mV. Panel C shows action potentials generated by the same cells in response to depolarizing stimuli. Cell membranes were held at voltages between −60 and −100 mV in −80 or −150 pA of current, and depolarized for short durations Example 6

Dopaminergic Cells Derived from Neural Drogenitor Cells

Embryoid bodies were cultured in suspension with 10 μM retinoic acid for 4 days, then plated into defined medium supplemented with EGF, bFGF, PDGF, and IGF-1 for 3-4 days. Cells were then separated by magnetic bead sorting or immunopanning into A2B5-positive or NCAM-positive enriched populations.

The immuno-selected cells were maintained in defined medium supplemented with 10 ng/mL NT-3 and 10 ng/mL BDNF. After 14 days, 25±4% of the NCAM-sorted cells were MAP-2 positive—of which 1.9 ±0.8% were GABA-positive, and 3±1% were positive for tyrosine hydroxylase (TH): the rate-limiting enzyme for dopamine synthesis, generally considered to be representative of dopamine-synthesizing cells.

In the cell population sorted for NCAM, the cells that were NCAM+ve did not express glial markers, such as GFAP or GalC. These data indicate that a population comprising neuron restricted precursors can be isolated directly from hES cell cultures, essentially uncontaminated with glial precursors.

Cells sorted for A2B5, on the other hand, have the capacity to generate both neurons and astrocytes. After the enrichment, the cells were placed into defined media supplemented with NT-3 and BDNF and allowed to differentiate for 14 days. Within the first 1-2 days after plating, cells in the A2B5 enriched population began to extend processes. After two weeks, cells took on the morphology of mature neurons, and 32±3% of the cells were MAP-2 positive. Importantly, 3±1% of the MAP-2 cells were TH-positive, while only 0.6±0.3% were GABA immunoreactive. These data indicate that a population of cells can be obtained from hES cells that comprise progenitors for both astrocytes and neurons, including those that synthesize dopamine.

Further elaboration of conditions for obtaining TH-expressing neurons was conducted as follows. Embryoid bodies were generated from confluent hES cells of the H7 line at passage 32 by incubating in 1 mg/mL collagenase (37° C., 5-20 min), scraping the dish, and placing the cells into non-adherent culture plates (Costar®). The resulting EBs were cultured in suspension in media containing FBS and 10 μM all-trans retinoic acid. After four days, the aggregates were collected and allowed to settle in a centrifuge tube. The supernatant was then aspirated, and the aggregates were plated onto poly L-lysine and fibronectin coated plates in proliferation medium (DMEM/F12 1:1 supplemented with N2, half-strength B27, 10 ng/mL EGF (R & D Systems), 10 ng/mL bFGF (Gibco), 1 ng/mL PDGF-AA (R & D Systems), and 1 ng/mL IGF-1 (R & D Systems).

The EBs were allowed to attach and proliferate for three days; then collected by trypsinizing ~1 min (Sigma) and plated at $1.5 \times 10^5$ cells/well onto poly I-lysine and laminin coated 4-well chamber slides in proliferation medium for one day. The medium was then changed to Neural Basal medium supplemented with B27, and one of the following growth cocktails:

10 ng/mL bFGF (Gibco), 10 ng/mL BDNF, and 10 ng/mL NT-3

10 ng/mL bFGF, 5000 ng/mL sonic hedgehog, and 100 ng/mL FGF8b 10 ng/mL bFGF alone The cells were maintained in these conditions for 6 days, with feeding every other day. On day 7, the medium was changed to Neural Basal medium with B27, supplemented with one of the following cocktails:

10 ng/mL BDNF, 10 ng/mL NT-3

1 μM cAMP, 200 μM ascorbic acid

1 μM cAMP, 200 μM ascorbic acid, 10 ng/mL BDNF, 10 ng/mL NT-3

The cultures were fed every other day until day 12 when they were fixed and labeled with anti-TH or MAP-2 for immunocytochemistry. Expression of the markers was quantified by counting four fields in each of three wells using a 40× objective lens.

Results are shown in Table 5. Initial culturing in bFGF, BDNF and NT-3 yielded the highest proportion of TH positive cells.

TABLE 5

Conditions for Producing Dopaminergic Neurons

| Culture conditions | | % of cells that are MAP-2 positive | % MAP-2 cells that are TH positive |
|---|---|---|---|
| days 1-6 | days 6-12 | | |
| BDNF, NT-3, bFGF | BDNF, NT-3 | 26% | 5.5% |
| BDNF, NT-3, bFGF | cAMP, AA (ascorbic acid) | 35% | 4.0% |
| BDNF, NT-3, bFGF | cAMP, AA, BDNF, NT-3 | 25% | 8.7% |
| bFGF, FGF8, SHH | BDNF, NT-3 | 37% | 3.7% |
| bFGF, FGF8, SHH | cAMP, AA | 34% | 3.9% |
| bFGF, FGF8, SHH | cAMP, AA, BDNF, NT-3 | 21% | 5.8% |
| bFGF | BDNF, NT-3 | 28% | 3.5% |
| bFGF | cAMP, AA | 26% | 4.1% |
| bFGF | cAMP, AA, BDNF, NT-3 | 22% | 5.7% |

Example 7

Increased Proportion of Dopaminergic Cells by Culturing with Erythropoietin

In a subsequent experiment, embryoid bodies were plated onto poly-lysine fibronectin coated wells, and cultured with 10 ng/mL EGF, 1 ng/mL PDGF-AA, 10 ng/mL bFGF, and 1 ng/mL IGF-1. On the fourth day, the mixture was supplemented with 5 U/mL EPO, 700 μM cAMP, or both. The cells were replated and treated for 7 days with 10 ng/mL BDNF, 10 ng/mL NT-3, and optionally EPO, cAMP, and 200 μM ascorbic acid. Results are shown in Table 6. The proportion of total cells in the culture that were MAP-2 positive was abnormally low in this experiment.

TABLE 6

Conditions for Producing Dopaminergic Neurons

| Culture Conditions | | | % MAP-2 cells that are | |
|---|---|---|---|---|
| days 1-3 | days 4-5 | days 6-12 | TH positive | (SD) |
| EGF, bFGF, PDGF, IGF-1 | EGF, bFGF, PDGF, IGF-1 | BDNF, NT-3 | 20% | (13%) |
| (same) | (same) | BDNF, NT-3, EPO, cAMP, AA | 24% | (3%) |
| (same) | same plus EPO | BDNF, NT-3, EPO, cAMP, AA | 31% | (13%) |
| (same) | same plus cAMP | BDNF, NT-3, EPO, cAMP, AA | 47% | (2%) |
| (same) | same plus EPO & cAMP | BDNF, NT-3, EPO, cAMP, AA | 57% | (7%) |

These data provide the first demonstration that adding cAMP and EPO during derivation of the neural precursor cells increases the percentage of neurons ultimately obtained that expressed tyrosine hydroxylase. Studer et al. reported that proliferation and differentiation of mesencephalic precursors in the presence of EPO or low partial pressures of $O_2$ result in higher numbers of dopaminergic neurons (J. Neurosci. 20:7377, 2000). EPO is thought to have a neuroprotective effect in hypoxic conditions, driving multipotent progenitors towards the neuronal pathway (Shingo et al., J. Neurosci. 21:9733, 2001). The effect may be a result of cross-talk between Janus kinase-2 and nuclear factor kappaB (NF-κB), upregulation of Bcl-x(L) expression, or activation of AP-1 (Jun/Fos) pathway. Regulating these pathways in pPS derived neural cells by other means may mimic the effects of EPO.

Example 8

Direct Differentiation of hES Cells

In a parallel series of experiments, differentiation was initiated not by forming embryoid bodies, but by plating undifferentiated hES cells directly onto a solid surface in the absence of feeder cells or other factors that inhibit differentiation.

Suspensions of rhesus and human ES cells were dissociated by trituration to clusters of ~50-100 cells, and plated onto glass coverslips treated with poly-ornithine. The cells were maintained in serum containing medium, or defined medium for 7-10 days before analysis. The cells were then tested by immunoreactivity for β-tubulin III and MAP-2, which are characteristic of neurons, and glial fibrillary acidic protein (GFAP), which is characteristic of astrocytes.

Several different ES lines were differentiated into cells bearing markers for neurons and astrocytes, using either the aggregate or direct differentiation technique. In cultures derived from rhesus ES cells, percentage of aggregates that contained neurons ranged from 49% to 93%. In cultures derived from human ES cells, the percentage of aggregates containing neurons ranged from 60% to 80%. Double labeling for GABA and β-tubulin indicated that a sub-population of the neurons express the inhibitory neurotransmitter GABA. Astrocytes and oligodendrocytes were identified with GFAP immune reactivity and GalC immune reactivity, respectively. Therefore, the human and rhesus ES cells have the capacity to form all three major cell phenotypes in the central nervous system.

The effect of several members of the neurotrophin growth factor family was examined. hES cells were differentiated by harvesting with collagenase, dissociating, and reseeding onto poly-ornithine coated cover slips. The cells were plated into DMEM/F12+N2+10% FBS overnight. The following day, the serum was removed from the medium and replaced with 10 ng/mL human bFGF and the growth factor being tested. After 24 hours, bFGF was removed from the medium. These cultures were fed every other day. They were fixed after 7 days of differentiation and immunostained for analysis. The number of neurons was evaluated by counting cells positive for β-tubulin. Cultures maintained in the presence of 10 ng/mL brain derived neurotrophic factor (BDNF) formed approximately 3-fold more neurons than the control cultures. Cultures maintained in neurotrophin-3 (1 ng/mL) formed approximately 2-fold more neurons than control cultures.

Example 9

Direct Differentiation of hES Cells to Dopaminergic Neurons

This study evaluated various paradigms for differentiating human ES cells into neurons without the formation of embryoid bodies.

A strategy was developed in which the test factors were placed into groups based on homology and/or functional redundancy (Table 3). Grouping factors increases the likelihood that an activity associated within that group will be elicited on the ES cell population. The hypothesis is that certain factors within the mixture will initiate a differentiation cascade. As differentiation proceeds, and the receptor expression profile of the cells change, they will become responsive to other factors in the mixture.

Providing a complex mixture of factors continuously over the treatment period avoids the need to define exactly how and when the responsiveness of the cells changes. When a mixture is identified that elicits the desired differentiation process, it can be systematically simplified to achieve a minimal optimal mixture. After further testing, minimal treatment may ultimately comprise one, two, three, or more of the factors listed, used either simultaneously or in sequence according to the empirically determined protocol.

TABLE 7

Test Factor Groups

| Group 1 Neurotrophins | Group 2 Mitogens | Group 3 Stem Cell Factors |
|---|---|---|
| 30 ng/mL NGF | 30 ng/mL EGF | 8 ng/mL LIF |
| 30 ng/mL NT-3 | 30 ng/mL FGF-2 (basic FGF) | 3 ng/mL IL-6 |
| 30 ng/mL NT-4 | 37 ng/mL FGF-8b | 3 ng/mL IL-11 |
| 30 ng/mL BDNF | 30 ng/mL IGF-1 | 3 ng/mL SCF |
|  | 30 ng/mL PDGF-AA | 30 ng/mL CNTF |

| Group 4 Differentiation Factors TGF-β Superfamily | Group 5 TGF-β Superfamily Antagonists | Group 6 Differentiation Factor |
|---|---|---|
| 30 ng/mL BMP-2 | 150 ng/mL Noggin | 37 ng/mL SHH |
| 37 ng/mL GDF-5 | 30 ng/mL Follistatin |  |
| 3 ng/mL GDNF |  |  |
| 30 ng/mL Neurturin |  |  |

| Group 7 Neurotrophic Factor | Group 8 Differentiation Factor | Group 9 Survival Factor/Antioxidant |
|---|---|---|
| 37 ng/mL Midkine | 17 μM Retinoic Acid | 166 μM Ascorbic Acid |

|  | Group 10 Differentiation Factor/ Neurotransmitter | Group 11 Survival Factor |
|---|---|---|
|  | 10 μM Dopamine | 100 μM Dibutyryl cAMP |

The experiment was conducted as follows. Monolayer cultures of a human ES cell line were harvested by incubating in Collagenase IV for 5-10 min, and then scraping the cells from the plate. The cells were dissociated by trituration and plated at subconfluence onto 96 well tissue culture plates pretreated with growth factor-reduced Matrigel® in Knockout DMEM medium (Gibco BRL) with Knockout Serum Replacement (Gibco BRL) conditioned 24 h by mouse embryonic feeder cells One day after plating, the medium was replaced with Neurobasal (NB) Medium (Gibco BRL) supplemented with 0.5 mM glutamine, B27 supplement (Gibco BRL) and groups of test factors as described below. The cells were fed daily with fresh Neurobasal Medium containing glutamine, B27, and test factors for 11 days.

After 11 days, the cells were harvested by incubation in trypsin for 5-10 min, replated at a 1:6 dilution onto 96 well tissue culture plates pretreated with laminin, and fed daily with fresh Neurobasal Medium containing glutamine, B27 and test factors for an additional 5 days. Cells were fixed for 20 min in 4% paraformaldehyde, and stained with antibodies to the early neuronal marker, β-Tubulin-III, the late neuronal marker, MAP-2, and tyrosine hydroxylase, an enzyme associated with dopaminergic neurons. Cell nuclei were labeled with DAPI, and quantified by visual inspection. Results are shown in Table 8.

TABLE 8

Direct Differentiation of hES Cells to Neurons

| Test Compound Groups Included in Cell Culture | βTubulin-III positive Cells/Well | % Total | MAP-2 positive Cells/Well | Tyrosine Hydroxylase positive Cells/Well | % Total |
|---|---|---|---|---|---|
| Control | 102 | — | 2 | 1 | — |
| Treatment A: 1, 2, 3, 4, 6, 7, 8, 9, 10, 11 | 0 | 0 | 0 | 0 | — |
| Treatment B: 1, 2, 3, 5, 6, 7, 8, 9, 10, 11 | 362 | 6% | 132 | 14 | 0.2% |
| Treatment C: 1, 2, 4, 6, 7, 8, 9, 10, 11 | — | — | — | — | — |
| Treatment D: 1, 2, 5, 6, 7, 8, 9, 10, 11 | 378 | 11% | 162 | 16 | 0.5% |
| Treatment E: 1, 3, 4, 6, 7, 8, 9, 10, 11 | 6 | — | 2 | 4 | — |
| Treatment F: 1, 3, 5, 6, 7, 8, 9, 10, 11 | 282 | 12% | 92 | 4 | 0.2% |
| Treatment G: 1, 4, 6, 7, 8, 9, 10, 11 | 17 | — | 0 | 2 | — |

— = not determined

In another experiment, cells were cultured in Neurobasal Medium supplemented with glutamine, B27 and groups of test factors as before, harvested with trypsin at 8 days, and replated for 5 days. Results are shown in Table 9.

TABLE 9

Direct Differentiation of hES Cells to Neurons

| Test Compound Groups Included in Cell Culture | βTubulin-III positive Cells/Well | MAP-2 positive Cells/Well | Tyrosine Hydroxylase positive Cells/Well | Percent of MAP-2 positive cells also positive for TH |
|---|---|---|---|---|
| Control | 4 | 4 | 0 | |
| Treatment 1, 2, 3, 4, 6, 7, 8, 9, 10, 11 A: | 12 | 8 | 3 | |
| Treatment 1, 2, 3, 5, 6, 7, 8, 9, 10, 11 B: | 268 | 12 | 4 | |
| Treatment 1, 2, 4, 6, 7, 8, 9, 10, 11 C: | 12 | 0 | 0 | |
| Treatment 1, 2, 5, 6, 7, 8, 9, 10, 11 D: | 372 | 48 | 7 | 15% |
| Treatment 1, 3, 4, 6, 7, 8, 9, 10, 11 E: | 0 | 0 | 0 | |
| Treatment 1, 3, 5, 6, 7, 8, 9, 10, 11 F: | 196 | 56 | 0 | |
| Treatment 1, 4, 6, 7, 8, 9, 10, 11 G: | 16 | 0 | 9 | |

Several treatment paradigms induced the direct differentiation of neurons. Treatments that included Group 5 factors (noggin and follistatin) were the most effective.

FIG. 5 shows exemplary fields of differentiated cells obtained using Treatment B, Treatment D, and Treatment F, and stained for β-tubulin-III. About 5-12% of the cells are neurons, based on morphology and β-tubulin-III staining. About ⅓ of these are mature neurons, based on MAP-2 staining. About 2-5% total neurons (5-15% of MAP-2 positive neurons) also stained for tyrosine hydroxylase, which is consistent with a dopaminergic phenotype.

Subsequent experiments have been conducted to further elucidate the effect of certain factor cocktails and the kinetics of differentiation.

FIG. 6(A) shows the results of an experiment in which the TGF-β superfamily antagonists noggin and follistatin were used for varying time periods. Subconfluent hES cells of the H7 line were treated for 15 days with Treatment D, except that cAMP concentration was 700 μg. The results indicate that noggin and follistatin both contribute to neuron differentiation, and work synergistically. Noggin is apparently important at about the 1 week point (days 5 to 8), while follistatin is important at around the 2 week point (days 13 to 15 maximizing production of mature neurons rather than small neurites.

FIG. 6(B) shows the time course of neuronal induction using the treatment mixtures in Table 8 containing TGF-β superfamily antagonists. FIG. 6(C) further illustrates the effects of noggin and follistatin in direct differentiation. hES cells represented by the first bar were treated with the factors of Groups 1, 4, 6, 7, 9, 10, and 11 (Table 7), with 700 μM cAMP, 5 U/mL EPO, plus 30 ng/mL FGF-8 (Group 2). Virtually7 no β-tubulin positive neurons were formed in the absence of noggin or follistatin. However, noggin and follistatin alone or in combination with retinoic acid directly induced hES cells through the first steps of neuronal differentiation. It is hypothesized that initial noggin/follistatin induction generates a neural progenitor cell, which subsequently can be induced to form neurons by the addition of other factors.

FIG. 6(D) shows the benefit of omitting retinoic acid (RA) from the mixture where dopaminergic neurons are desired. Cells were differentiated according to treatment F as previously (left 2 bars) or omitting retinoic acid (right 2 bars). Including retinoic acid increased the total percentage of β-tubulin positive neurons somewhat, but decreased the proportion of those neurons staining positively for tyrosine hydroxylase.

Example 10

Proliferative Regeneration of Neural Precursors by Serial Passging

The neural progenitors of this invention can be passaged and expanded in culture, demonstrating some of their unique and beneficial properties.

In an exemplary experiment, human embryonic stem cells were harvested and placed into suspension culture to form embryoid bodies in knockout DMEM containing 20% FBS plus 10 μM retinoic acid. After 4 days, the embryoid bodies were plated onto poly-L-lysine/fibronectin-coated plates in DMEM/F12 medium supplemented with N2 supplement, B27 supplement at half the usual amount, 10 ng/mL human EGF, 10 ng/mL human bFGF, 1 ng/mL human PDGF-AA, and 1 ng/mL human IGF-1.

The cells were cultured for 3 days, and harvested by brief trypsinization as follows. Half a mL 0.5% Trypsin in 0.53 mM EDTA (Gibco # 25300-054) was layered into each well of a 6-well plate, then immediately removed from the plate. After waiting 15 seconds (room temperature), neurobasal medium plus B27 supplement was placed in the wells, and then removed and centrifuged to recover the released cells (between 1 and 10% of the cells).

Six-well plates were coated with 1 mL/well of 15 μg/mL poly-L-lysine (Sigma #P1274), followed by 1 mL/well of 20

μg/mL human placental laminin (Gibco # 23017-015) overnight. The cell pellet from the differential trypsinization was resuspended in neurobasal medium containing B27 supplement, 10 ng/mL NT-3, and 10 ng/mL BDNF, and plated onto the coated wells at 500,000 to 750,000 cells per well.

After 5 days, the cells were recovered by complete trypsinization, counted, and replated at 100,000 to 150,000 cells per well in new poly-lysine/laminin coated wells in the presence of various factor cocktails. Concentrations used were as follows: 10 ng/mL NT-3, 10 ng/mL BDNF, 10 ng/mL human EGF, 10 ng/mL human bFGF, or 10 ng/mL LIF, in various combinations. The cells were fed with a half exchange of medium three times per week. Every 7 days, the cells were trypsinized, counted, and passaged again in fresh medium containing the same factors.

FIG. 7(A) shows the growth curves from this experiment. Cells passaged in BDNF and NT-3 alone stop growing after ~1 week, predominantly differentiating into neurons. However, adding EGF and bFGF to the medium allowed the cells to continue proliferating in the precursor form. The marker profile of these cells is shown in Table 10.

In a related experiment, cells were grown and passaged as clusters rather than on a culture substrate. Neural progenitors were harvested using trypsin from a 6 well plate when nearly confluent (~3 or 4×10$^5$ cells per well). They were then seeded at ~2.5×10$^5$ cells per well in nonadherent wells, and cultured in 2 mL neural basal medium containing B27 supplement, 10 ng/mL BDNF, 10 ng/mL NT-3, 10 ng/mL EGF, and 10 ng/mL bFGF. The cells were fed the following day by exchanging half the medium, and cultured for a following 4 days. They were then differentiated in medium containing 10 ng/mL BDNF and 10 ng/mL NT-3 but no mitogens.

Adaptations of the invention described in this disclosure are a matter of routine optimization, and can be done without departing from the spirit of the invention, or the scope of the claims below.

What is claimed as the invention is:

1. A method of screening a compound for its effect on neural cells or a neural cell activity, comprising:
   a) obtaining from an established line of primate pluripotent stem (pPS) cells a population of cells wherein at

TABLE 10

Phenotype of Neural Progenitors

| Cocktail | Passage | Nestin | PS-NCAM | A2B5 | β-tubulin III | GFAP | MAP2 | Tyrosine Hydroxylase |
|---|---|---|---|---|---|---|---|---|
| NT-3, BDNF, | p4 | +++ | +++ | ++ | + | + | − | − |
| EGF, bFGF, LIF | p8 | +++ | +++ | + | + | + | − | − |
| NT-3, BDNF, | p4 | +++ | +++ | + | + | + | − | − |
| EGF, bFGF | p8 | +++ | +++ | − | + | + | − | − |
| EGF, bFGF, LIF | p4 | ++ | ++ | + | + | + | − | − |
| | p8 | ++ | ++ | − | + | − | − | − |
| EGF, bFGF | p4 | ++ | ++ | − | − | − | − | − |
| | p8 | + | + | − | − | − | − | − |

Thus, cells passaged in a combination of BDNF, NT-3, EGF, and bFGF abundantly expressed the neural progenitor markers Nestin and NCAM.

Figure 1:
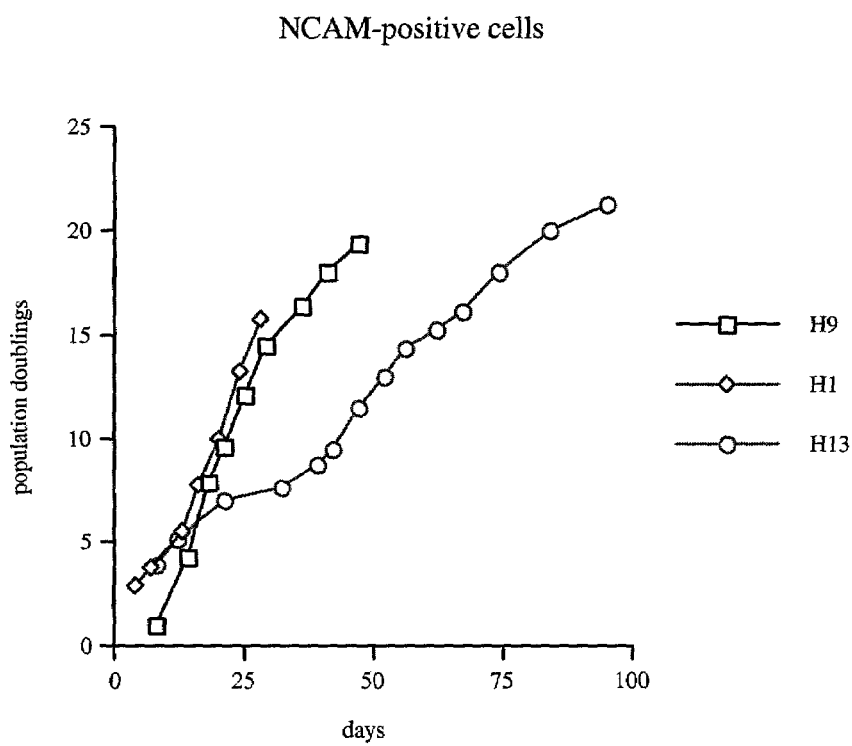
Figure 1:
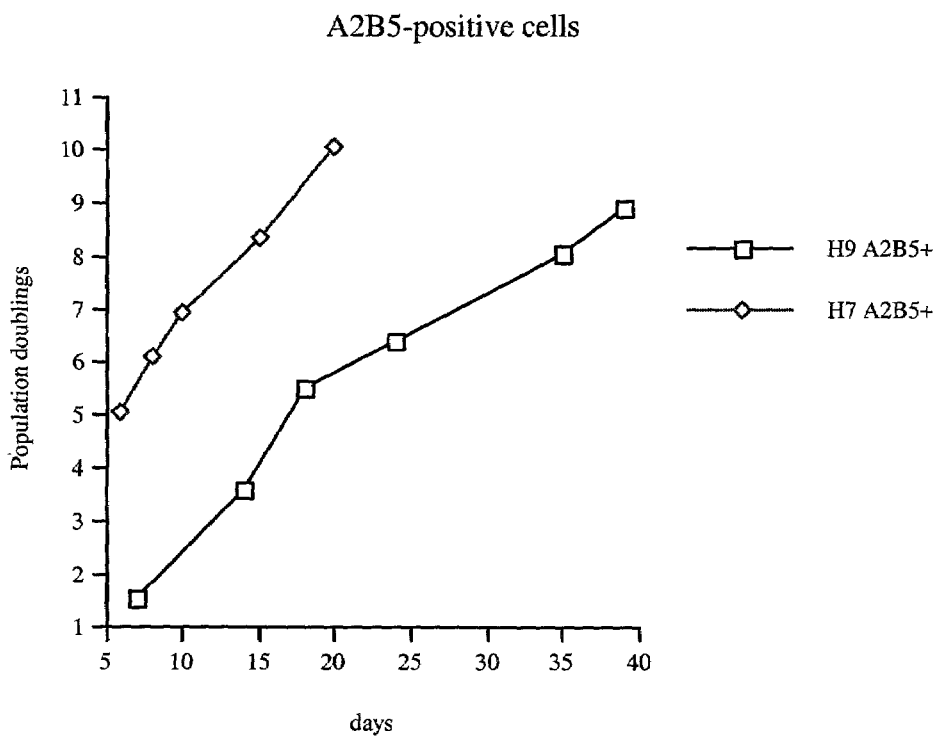
Figure 2:
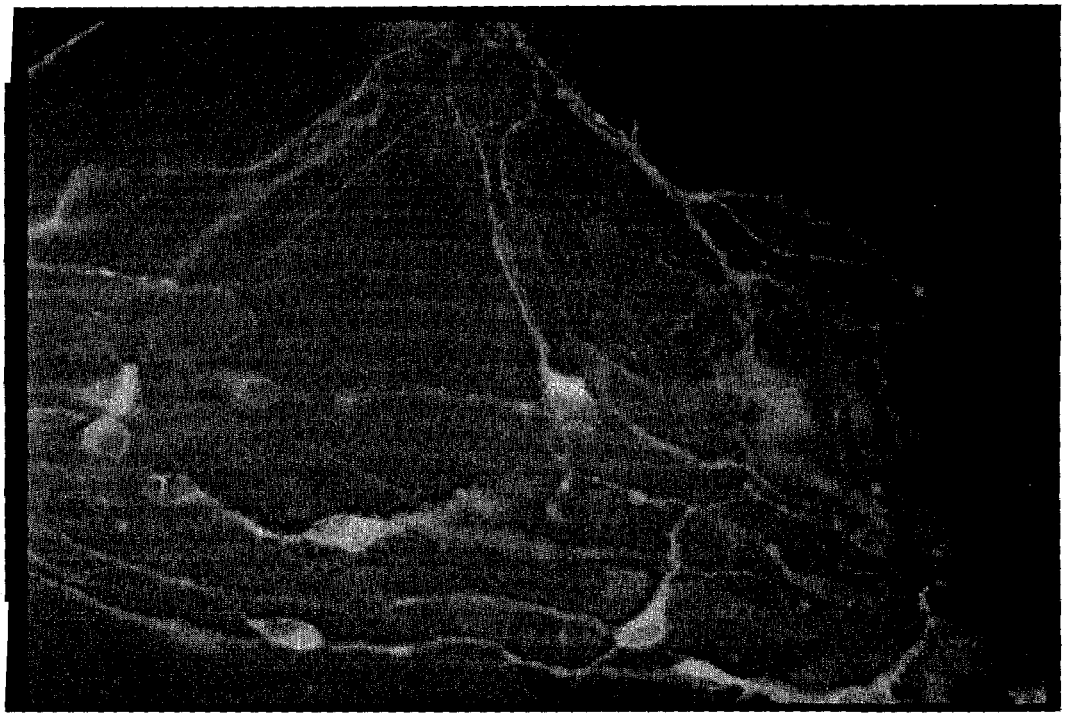
Figure 3:
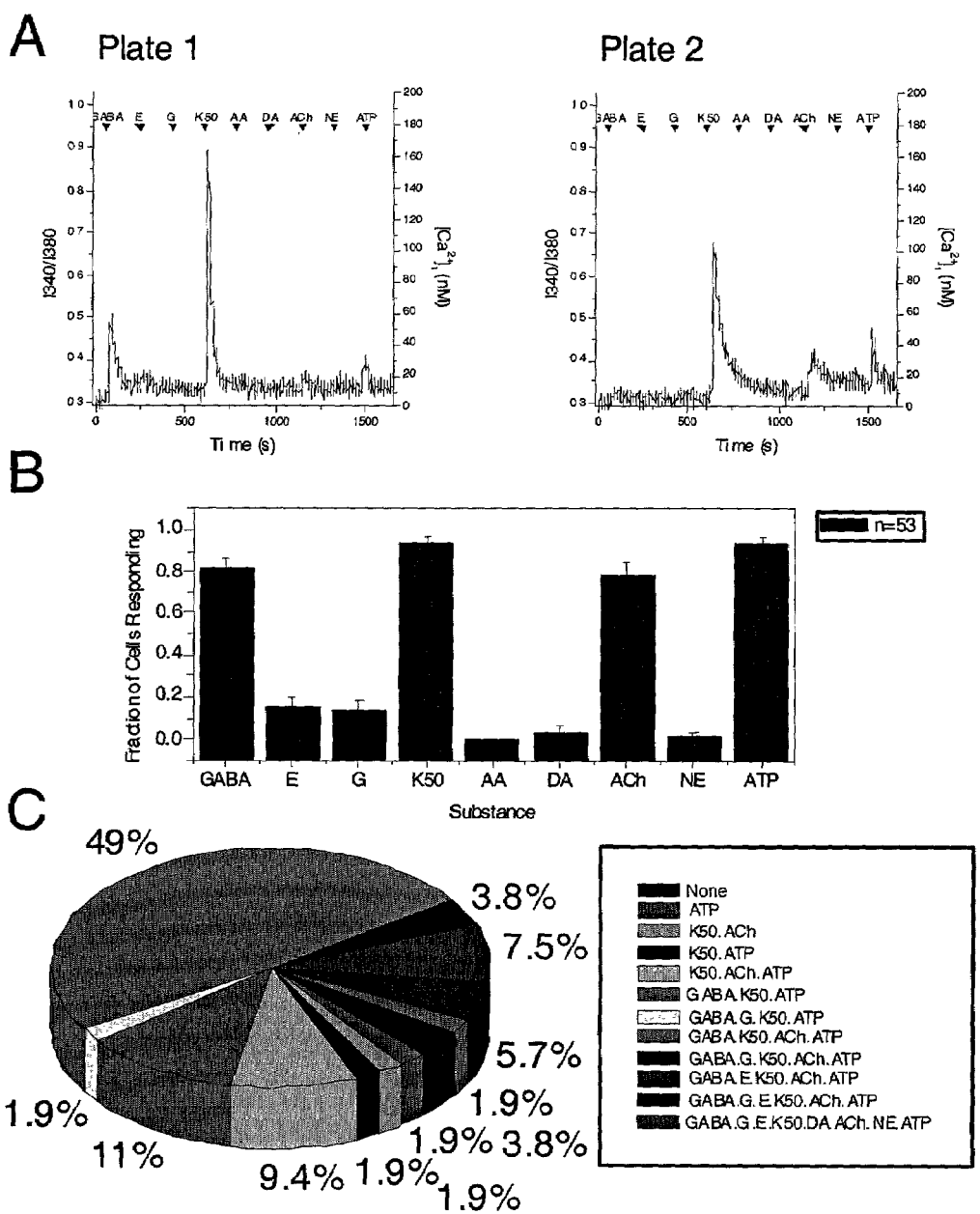
Figure 4:
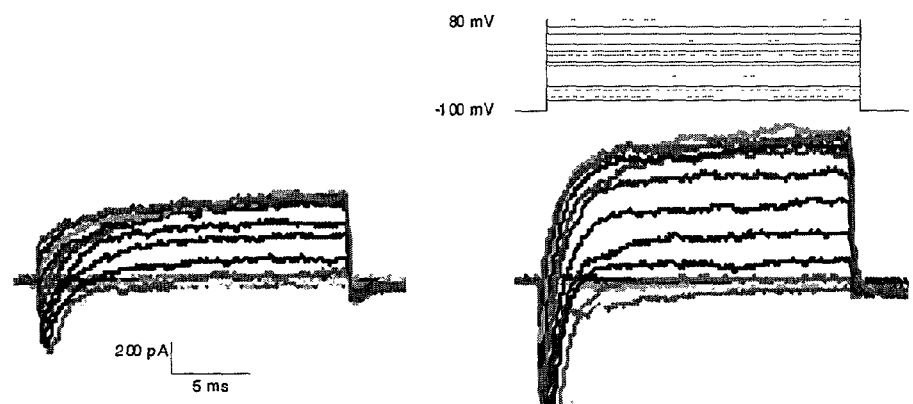
Figure 4:
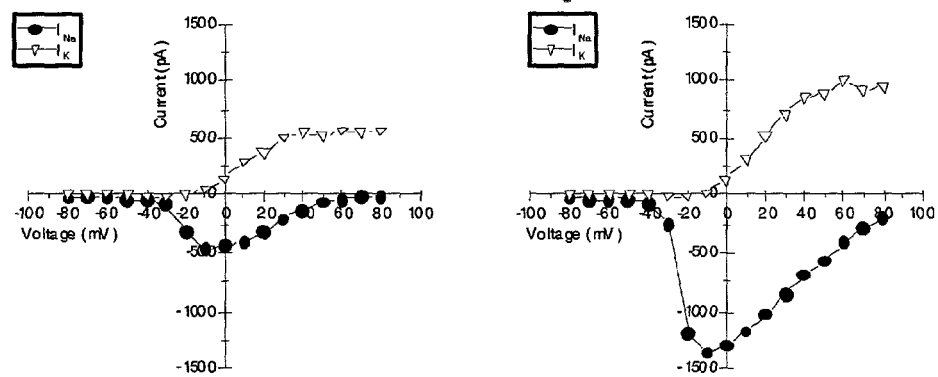
Figure 4:
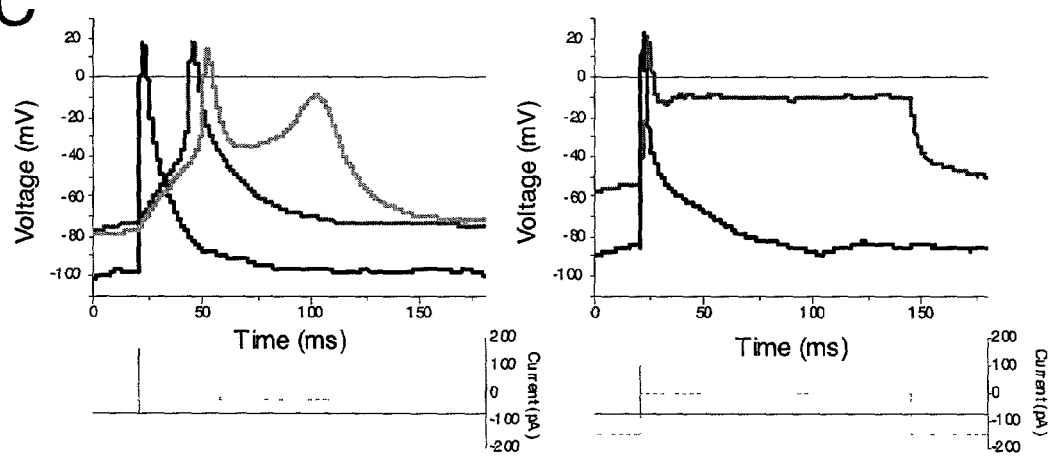
Figure 5:
Figure 5:
Figure 5:
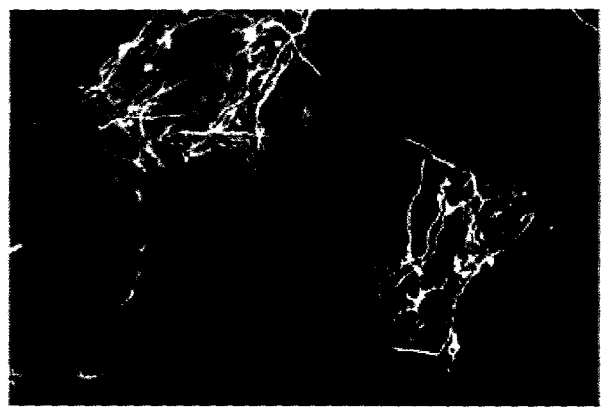
Figure 6:
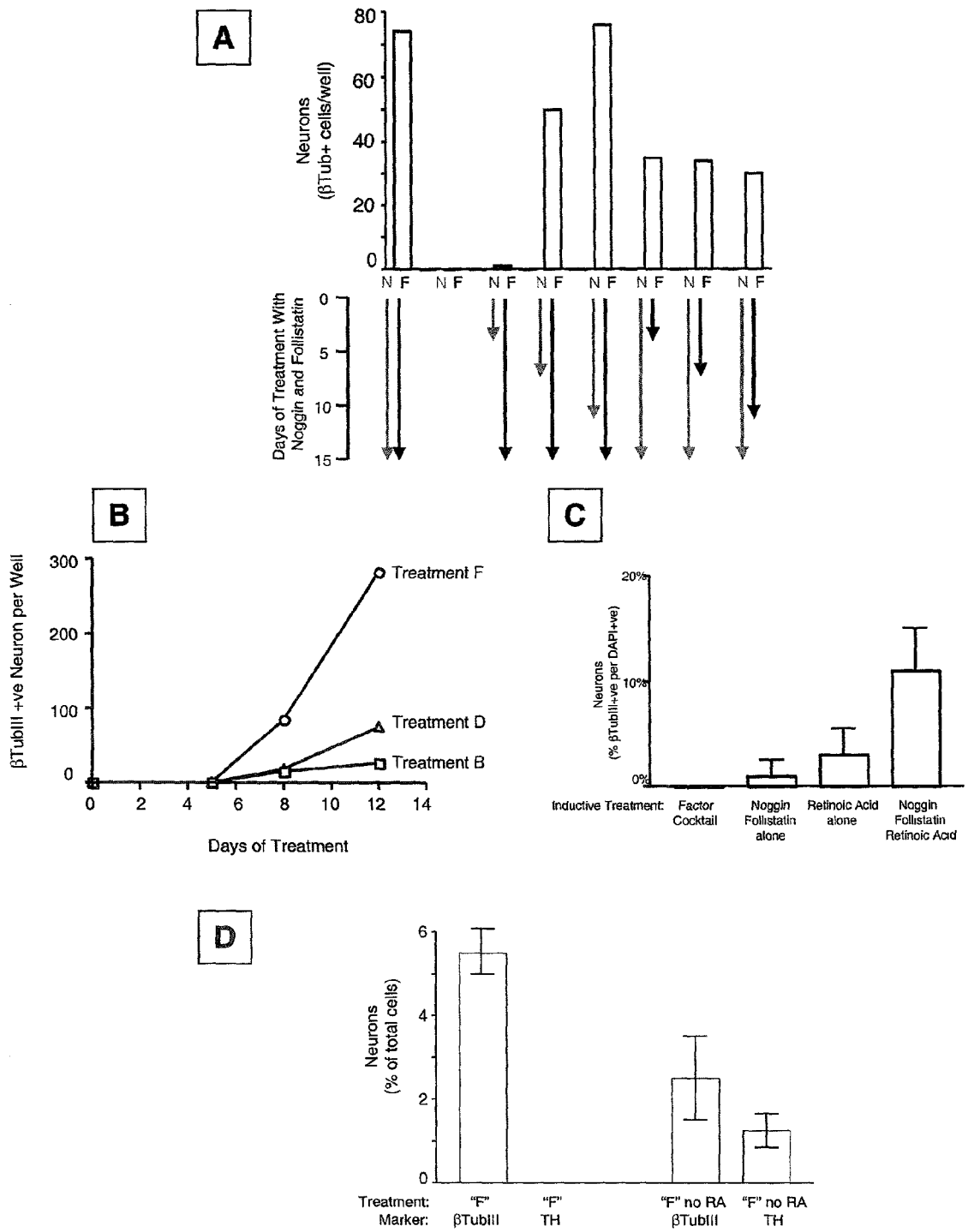
Figure 7:
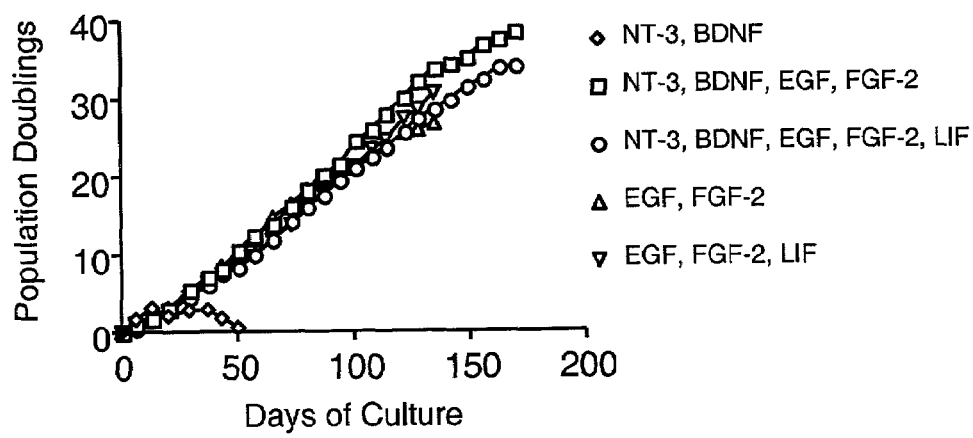
FIG. 7(B) shows results obtained when these cells were induced to terminally differentiate in BDNF and NT-3 alone. The cells passaged in a combination of BDNF, NT-3, EGF and bFGF produced more neurons upon terminal differentiation, consistent with the higher proportion of neural precursors before differentiation.
Figure 7:
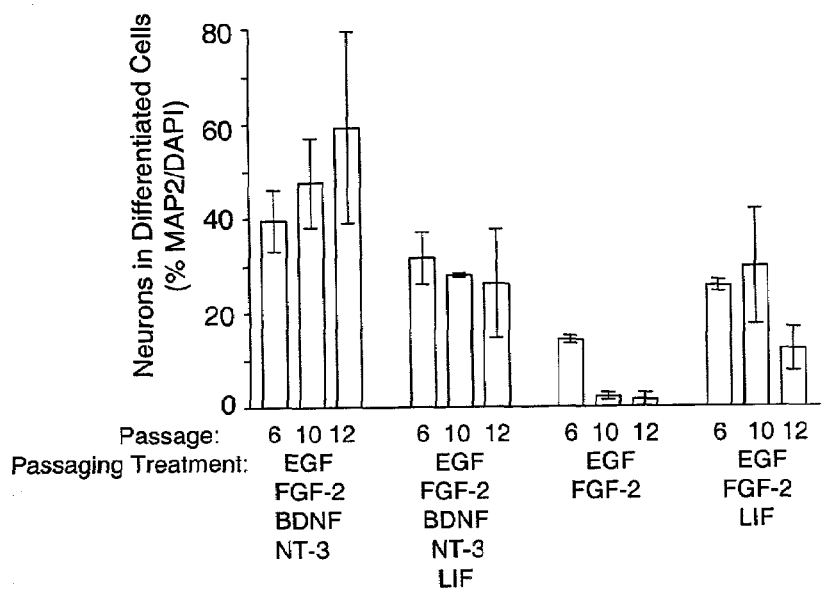
Figure 8:
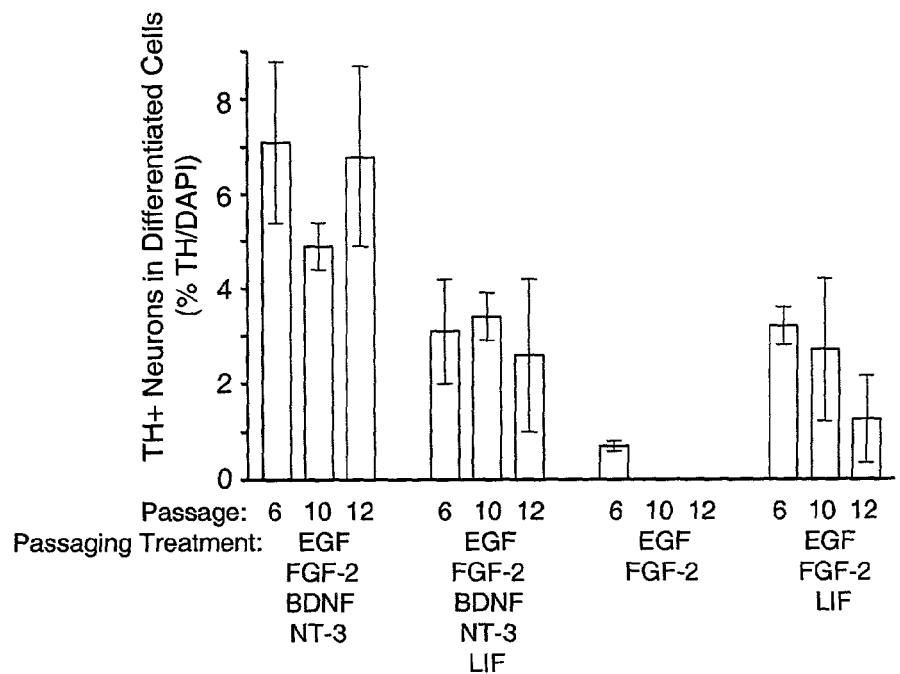
FIG. 8(A) shows the proportion of cells staining positively for tyrosine hydroxylase. Again, the combination of BDNF, NT-3, EGF and bFGF provided optimal yield amongst the combinations tested.
FIG. 8(B) shows that even more TH-positive neurons can be generated by inducing terminal differentiation not by BDNF and NT-3 alone, but also including additional factors such as NT-4, nerve growth factor, ascorbic acid, cAMP and dopamine (at the concentrations shown in Table 7). Up to 5% of the total cell number in the population displayed the phenotype of dopaminergic markers.
Figure 8:
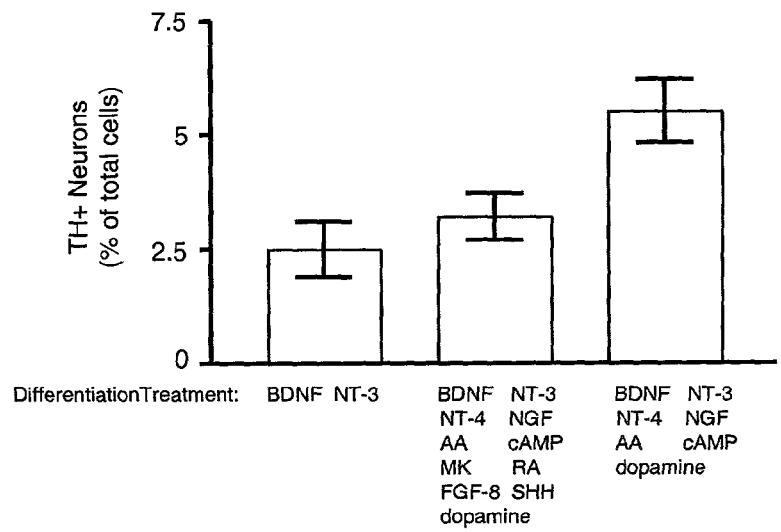

Neural progenitors from the H7 hES cell line were frozen down at passage 10 in neural basal medium containing B27 supplement, 30% serum replacement, and 10% DMSO (5×10$^6$ cells per freezing vial). The cells were thawed about 6.5 months later. The thawed cells had many of the same characteristics that they did before freezing: 60-80% β-tubulin and MAP-2 positive, ~5% positive for tyrosine hydroxylase.

least 75% of the cells are characterized as cells of the neuronal lineage by the criterion that they express polysialylated NCAM;
   b) combining the cell population with the compound;
   c) determining any change to phenotype or activity of cells in the population that results from being combined with the compound; and
   d) correlating the change with an effect of the compound on neural cells or a neural cell activity.

2. The method of claim 1, comprising determining whether the compound is toxic to cells in the population.

3. The method of claim 1, comprising determining whether the compound affects ability of cells in the population to be maintained in culture.

4. The method of claim 1, comprising determining whether the compound changes neurotransmitter synthesis, release, or uptake by cells in the population.

5. The method of claim 1, comprising determining whether the compound changes electrophysiology of cells in the population.

6. The method of claim 1, wherein the pPS cells are human embryonic stem cells.

7. The method of claim 1, wherein the cell population was produced by a process that comprised culturing progeny of the pPS cells in a medium containing one or more added TGF-β superfamily antagonists.

8. The method of claim 7, wherein process comprised initiating differentiation of the pPS cells by plating onto a solid surface without forming embryoid bodies or cell aggregates.

9. The method of claim 7, wherein the process comprised culturing progeny of the pPS cells in a medium containing both noggin and follistatin.

10. The method of claim 1, wherein the cell population was produced by culturing progeny of the pPS cells in a medium containing one or more added mitogens and one or more added neurotrophins.

11. The method of claim 10, wherein the cell population was produced by pre-differentiating pPS cells by forming embryoid bodies before culturing with the neurotrophins and mitogens.

12. The method of claim 10, wherein the cell population was produced by culturing the cells with one or more added mitogens before culturing with the neurotrophins.

13. The method of claim 10, wherein the added mitogen(s) include a mitogen selected from epidermal growth factor (EGF), basic fibroblast growth factor (bFGF), platelet-derived growth factor (PDGF), and insulin-like growth factor 1 (IGF-1), and the added neurotrophins include neurotrophin 3 (NT-3) or brain-derived neurotrophic factor (BDNF).

14. The method of claim 10, wherein the added mitogen(s) include erythropoietin (EPO).

15. The method of claim 10, wherein the cell population was produced by passaging the cells at least 6 times in a medium comprising an added neurotrophin and an added mitogen.

16. The method of claim 1, wherein the cell population has been terminally differentiated by culturing progeny of the pPS cells in a medium containing one or more factors selected from neurotrophins, cAMP, and ascorbic acid in the absence of added mitogens.

* * * * *